United States Patent
Wu et al.

(10) Patent No.: US 10,822,365 B1
(45) Date of Patent: Nov. 3, 2020

(54) SGLTS INHIBITOR AND APPLICATION THEREOF

(71) Applicant: SHANDONG DANHONG PHARMACEUTICAL CO., LTD., Heze (CN)

(72) Inventors: Chengde Wu, Shanghai (CN); Qinghua Mao, Shanghai (CN); Yi Li, Shanghai (CN); Tao Yu, Shanghai (CN); Shuhui Chen, Shanghai (CN)

(*) Notice: Subject to any disclaimer, the term of this patent is extended or adjusted under 35 U.S.C. 154(b) by 0 days.

(21) Appl. No.: 16/916,108

(22) Filed: Jun. 30, 2020

Related U.S. Application Data

(63) Continuation of application No. PCT/CN2019/070336, filed on Jan. 4, 2019.

(30) Foreign Application Priority Data

Jan. 5, 2018 (CN) .......................... 2018 1 0012284

(51) Int. Cl.
*C07H 15/14* (2006.01)
*A61P 3/10* (2006.01)

(52) U.S. Cl.
CPC .............. *C07H 15/14* (2013.01); *A61P 3/10* (2018.01)

(58) Field of Classification Search
None
See application file for complete search history.

(56) References Cited

U.S. PATENT DOCUMENTS

| | | |
|---|---|---|
| 2010/0311673 A1 | 12/2010 | Harrison et al. |
| 2012/0172320 A1 | 7/2012 | Chen et al. |
| 2013/0225514 A1 | 8/2013 | Luo |
| 2016/0222047 A1 | 8/2016 | Zhong et al. |

FOREIGN PATENT DOCUMENTS

| | | |
|---|---|---|
| CN | 101503399 A | 8/2009 |
| CN | 102146066 A | 8/2011 |
| CN | 104109154 A | 10/2014 |
| WO | 2008042688 A2 | 4/2008 |

OTHER PUBLICATIONS

Internatinal Search Report of PCT/CN2019/070336, dated Mar. 27, 2019.

*Primary Examiner* — Po-Chih Chen
(74) *Attorney, Agent, or Firm* — W&K IP

(57) ABSTRACT

A compound as an SGLT1/SGLT2 dual inhibitor, and an application thereof in the preparation of a drug as the SGLT1/SGLT2 dual inhibitor. The compound is a compound represented by formula (I), an isomer thereof, or a pharmaceutically acceptable salt thereof.

(I)

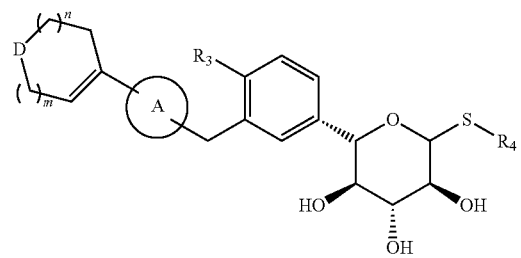

13 Claims, 2 Drawing Sheets

SGLTS INHIBITOR AND APPLICATION THEREOF

CROSS-REFERENCE TO RELATED APPLICATIONS

This application is a continuation of International Patent Application No. PCT/CN2019/070336 with a filing date of Jan. 4, 2019, designating the United States, now pending, and claims priority to Chinese Patent Application No. 201810012284.4 with a filing date of Jan. 5, 2018. The content of the aforementioned applications, including any intervening amendments thereto, are incorporated herein by reference.

TECHNICAL FIELD

The present invention relates to a compound as an SGLT1/SGLT2 dual inhibitor, and an application thereof in the preparation of a drug as the SGLT1/SGLT2 dual inhibitor. Specifically, the compound is a compound represented by formula (I), an isomer thereof, or a pharmaceutically acceptable salt thereof.

BACKGROUND

Diabetes is a metabolic disease characterized by hyperglycemia. Hyperglycemia is caused by deficiency of insulin secretion and/or damage of biological function. In patients with diabetes, long-term abnormal blood glucose levels can lead to serious complications, including cardiovascular disease, chronic renal failure, retinal injury, nerve injury, microvascular injury and obesity or like. In the early stage of the treatment of diabetes, diet control and exercise therapy are the preferred methods for blood glucose control. When these methods do not work, insulin or oral hypoglycemic drugs are required for the treatment. At present, various hypoglycemic drugs, including biguanides, sulfonylureas, insulin resistance improvers, glinides, α-glucosidase inhibitors, dipeptidyl peptidase-IV inhibitors and the like, are used in clinical treatment. These drugs have good therapeutic effects, but also have safety problems in the long-term treatment. For example, biguanides may cause lactic acidosis, sulfonylureas may cause hypoglycemia, insulin resistance improvers may cause edema, heart failure and weight gain, and α-glucosidase inhibitors may cause symptoms including abdominal pain, abdominal distension, diarrhea or like. Therefore, there is an urgent need to develop a safer and more effective new hypoglycemic drug to meet the needs of the treatment of diabetes.

Sodium-glucose cotransporters (SGLTs) are a family of glucose transporters found in the small intestinal mucosa and renal proximal convoluted tubules. The family mainly comprises two members including SGLT1 proteins and SGLT2 proteins which mediate the transmembrane transport of glucose in the intestine and kidney and play a key role in maintaining the stability of human blood glucose. Specifically, SGLT1 is distributed mainly in intestinal mucosal cells of the small intestine and is also expressed in a small amount in myocardium and kidney, and mainly regulates the absorption of glucose in the intestine. SGLT2 is expressed at a high level in the kidney, mainly responsible for the regulation of glucose reuptake in the kidney, that is, when glucose in urine is filtered through glomerulus, it can be actively attached to renal tubular epithelial cells and transported into cells through SGLT2 protein so that the glucose can be reused. In this process, SGLT2 is responsible for the reabsorption of 90% glucose, and the reabsorption of the remaining 10% is done by SGLT1. This process is not involved in glucose metabolism, thus avoiding or reducing the occurrence of adverse reactions of hypoglycemia, and further reducing the risk of cardiovascular diseases. Therefore, SGLTs has become one of the ideal potential targets for the treatment of diabetes.

In view of this, some SGLTs inhibitors, especially highly selective SGLT2 inhibitors, have been developed successively. These inhibitors inhibit the activity of SGLT2, and thereby specifically inhibit the reabsorption of glucose by the kidney, thus increasing the excretion of glucose in urine and normalizing plasma glucose in patients with diabetes. Since 2012, six drugs including Dapagliflozin, Canagliflozin, Luseogliflozin, Ipragliflozin, Tofogliflozin and Empagliflozin have been approved for marketing and have become effective drugs for the treatment of diabetes.

In addition to use of selective SGLT2 inhibitors, recent studies have shown that inhibition of SGLT2 and partial inhibition of SGLT1 can not only inhibit glucose reuptake in the kidney, but also control the absorption of glucose in the intestine without diarrhea or other gastrointestinal reactions. Furthermore, it is found that inhibition of SGLT1 in the intestine can reduce the amount of glucose entering the blood from the gastrointestinal tract, increase levels of GLP-1 and PYY after meals, show a better hypoglycemic effect than selective SGLT2 inhibitors and can reduce the risk of urinary tract infection and renal function damage. Therefore, the development of SGLT1/SGLT2 dual inhibitor has become a new target and direction for the treatment of diabetes in recent years.

In summary, as a new type drug for the treatment of diabetes, the SGLT1/SGLT2 dual inhibitor has a good development prospect. Therefore, there is an urgent need to develop a SGLT1/SGLT2 dual inhibitor with excellent efficacy, good pharmacokinetics and high safety for the treatment of diabetes and related metabolic disorders. At present, Lexicon and Sanofi have jointly developed a SGLT1/SGLT2 dual inhibitor named Sotagliflozin and the Phase III clinical study has been completed (WO2008042688/WO2012094293).

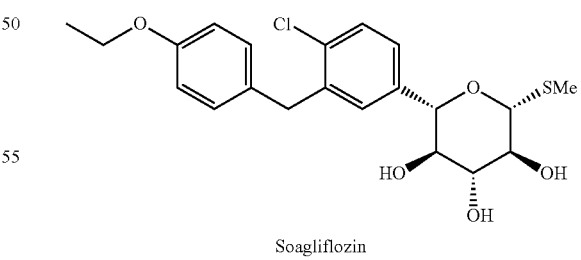

Soagliflozin

SUMMARY

The present disclosure provides a compound represented by formula (I), an isomer thereof, or a pharmaceutically acceptable salt thereof,

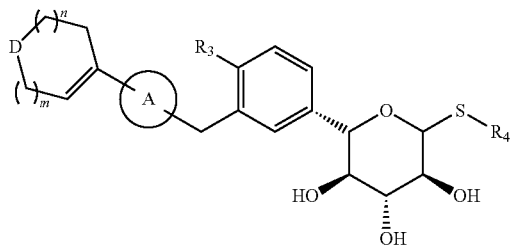

(I)

wherein, m is 1 or 2;
n is 0, 1 or 2;
D is —O— or —C($R_1$)($R_2$)—;
ring A is selected from phenyl and 5-6 membered heteroaryl;
$R_1$ is selected from the group consisting of H, F, Cl, Br, I, OH and $NH_2$;
$R_2$ is selected from the group consisting of H, F, Cl, Br and I;
or $R_1$ and $R_2$ are connected to form a 5-6 membered heterocycloalkyl;
$R_3$ is selected from the group consisting of H, F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by one, two or three R group(s);
$R_4$ is selected from $C_{1-3}$ alkyl, wherein the $C_{1-3}$ alkyl is optionally substituted by one, two or three R group(s);
R is selected from the group consisting of F, Cl, Br, I, OH and $NH_2$; and
the 5-6 membered heteroaryl and 5-6 membered heterocycloalkyl respectively contain one, two, three or four heteroatom(s) or heteroatom group(s) independently selected from the group consisting of —NH—, —O—, —S— and N.

In some embodiments of the present disclosure, the above $R_3$ is selected from the group consisting of H, F, Cl, Br, I, OH, $NH_2$, $CH_3$, Et, and —O—$CH_3$. Other variables are as defined by the present disclosure.

In some embodiments of the present disclosure, the above $R_4$ is selected from $CH_3$ and Et. Other variables are as defined by the present disclosure.

In some embodiments of the present disclosure, the above ring A is selected from phenyl and thienyl. Other variables are as defined by the present disclosure.

In some embodiments of the present disclosure, the above ring A is selected from

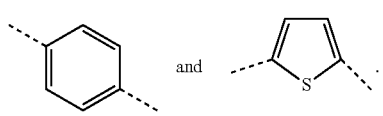

Other variables are as defined by the present disclosure.

In some embodiments of the present disclosure, the above structural unit

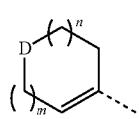

is selected from

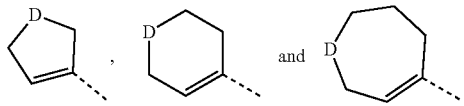

Other variables areas defined by the present disclosure.

In some embodiments of the present disclosure, the above structural unit

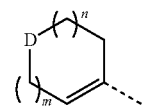

is selected from

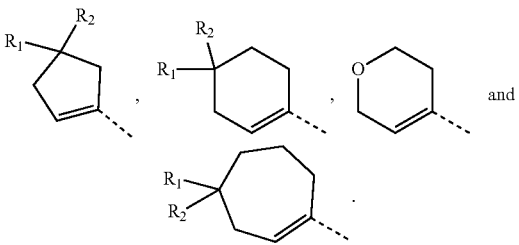

Other variables are as defined by the present disclosure.

In some embodiments of the present disclosure, the above structural unit

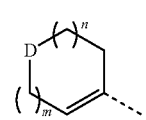

is selected from

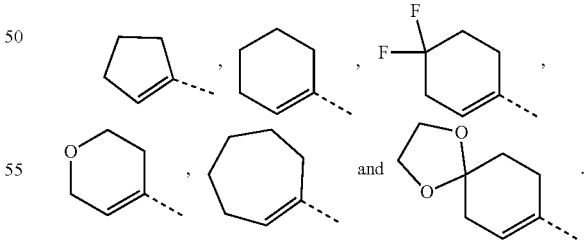

Other variables are as defined by the present disclosure.

Some embodiments of the present disclosure are derived from any combination of the above variables.

In some embodiments of the present disclosure, the above compound, the isomer thereof, or the pharmaceutically acceptable salt thereof is selected from the group consisting of (I-1)
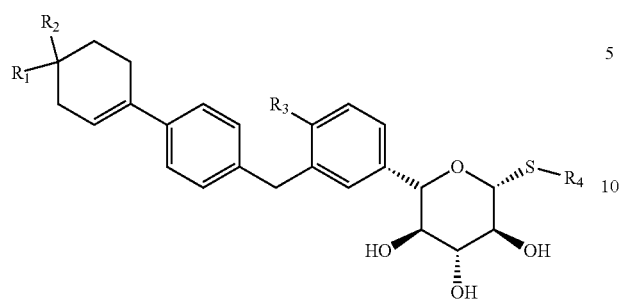
(I-2)
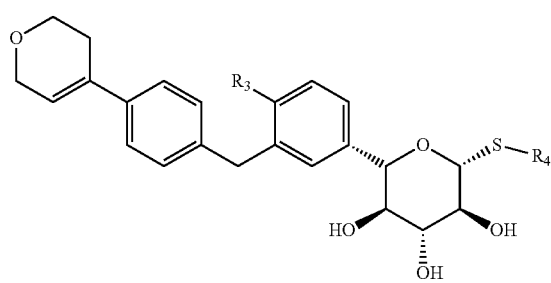
(I-3)
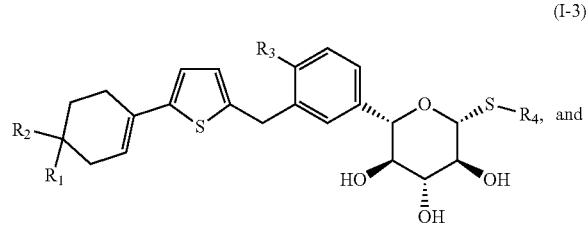
(I-4)
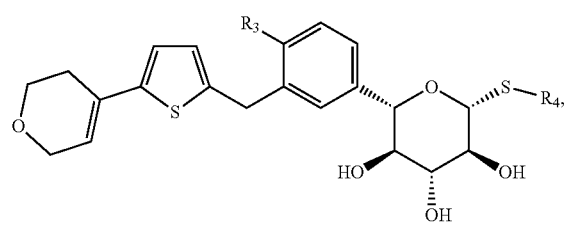
wherein,
R₁, R₂, R₃ and R₄ are as defined in the present disclosure.
The present disclosure provides a compound of the following formula an isomer thereof, or a pharmaceutically acceptable salt thereof, selected from
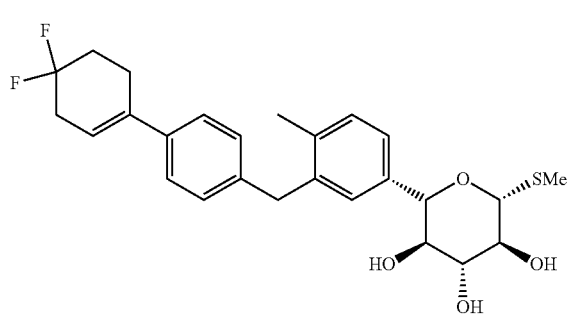
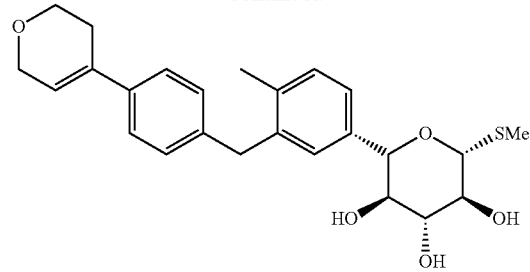
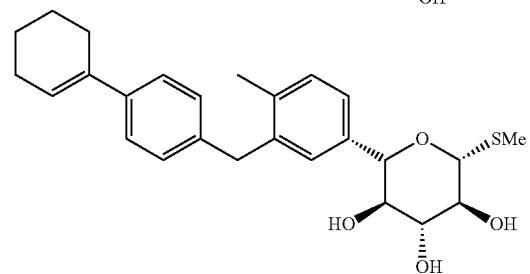
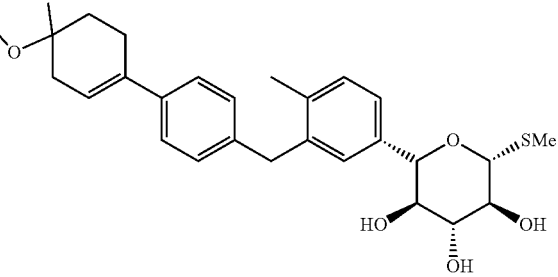
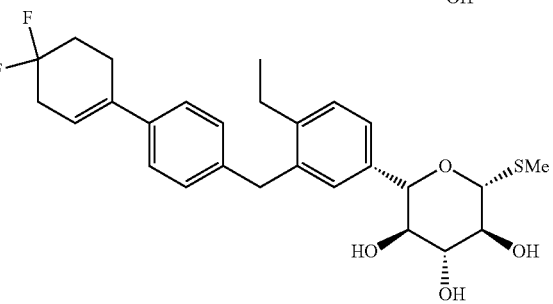
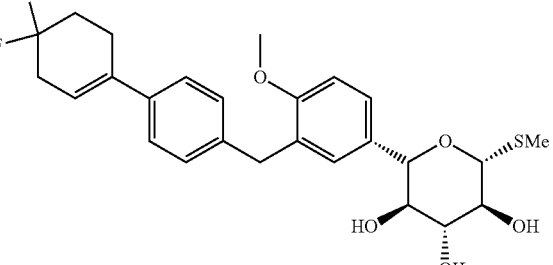
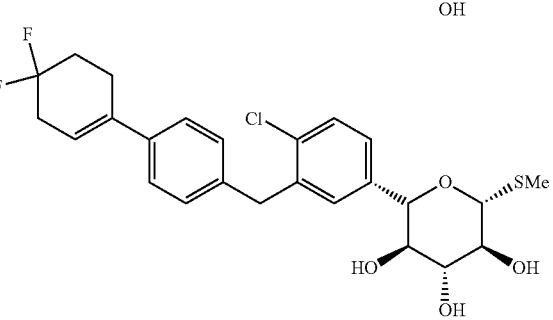

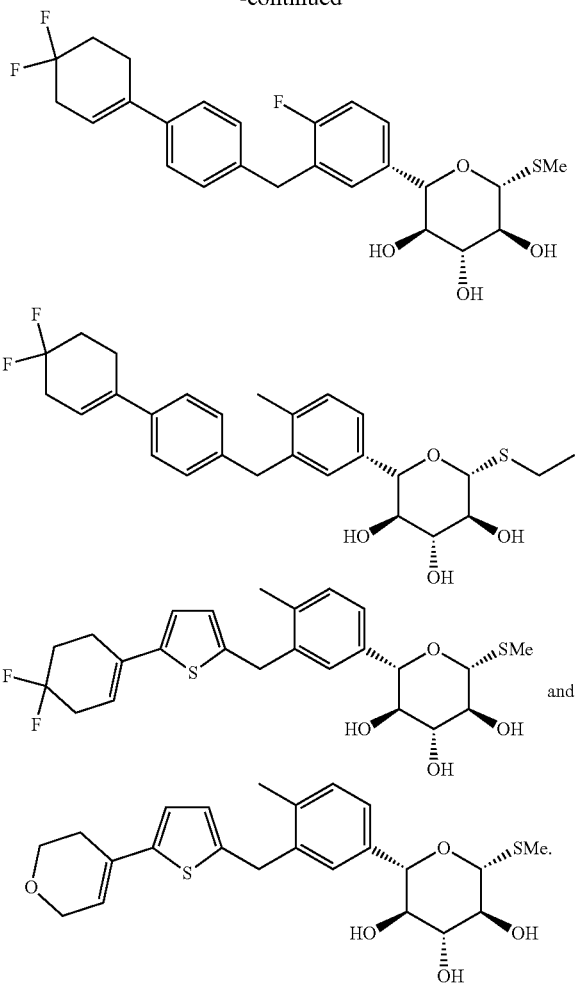

The present disclosure provides a pharmaceutical composition, comprising a therapeutically effective amount of the above compound, the isomer thereof or the pharmaceutically acceptable salt thereof as an active ingredient, and a pharmaceutically acceptable carrier.

The present disclosure provides use of the above compound or the pharmaceutically acceptable salt thereof or the above pharmaceutical composition in the manufacture of a medicament for treating SGLT1/SGLT2 related diseases.

In some embodiments of the present disclosure, the disease is diabetes.

Technical Effect

The compound of the present disclosure exhibits superior inhibitory activity against Human-SGLT1 and Human-SGLT2 in vitro, and exhibits good hypoglycemic effect in animals.

Definition and Description

Unless otherwise stated, the following terms and phrases as used herein are intended to have the following meanings. A particular term or phrase should not be considered undefined or unclear without a particular definition, but should be understood in the ordinary sense. When a trade name appears herein, it is intended to refer to its corresponding commodity or its active ingredient. The term "pharmaceutically acceptable" as used herein is intended to mean that those compounds, materials, compositions and/or dosage forms are within the scope of sound medical judgment and are suitable for use in contact with human and animal tissues without excessive toxicity, irritation, allergic reactions or other problems or complications, and commensurate with a reasonable benefit/risk ratio.

The term "pharmaceutically acceptable salt" refers to a salt of the compound of the present disclosure, prepared from a compound having a particular substituent found in the present disclosure and a relatively non-toxic acid or base. When a relatively acidic functional group is contained in the compound of the present disclosure, a base addition salt can be obtained by contacting a neutral form of such a compound with a sufficient amount of a base in a pure solution or a suitable inert solvent. Pharmaceutically acceptable base addition salts include sodium salts, potassium salts, calcium salts, ammonium salts, organic amine salts or magnesium salts or similar salts. When a relatively basic functional group is contained in the compound of the present disclosure, an acid addition salt can be obtained by contacting a neutral form of such a compound with a sufficient amount of an acid in a pure solution or a suitable inert solvent. Examples of pharmaceutically acceptable acid addition salts include inorganic acid salts, wherein the inorganic acid includes, for example, hydrochloric acid, hydrobromic acid, nitric acid, carbonic acid, hydrogen carbonate, phosphoric acid, monohydrogen phosphate, dihydrogen phosphate, sulfuric acid, hydrogen sulfate, hydroiodic acid, and phosphorous acid; and organic acid salts, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and further include salts of amino acids (such as arginine, etc.), and salts of organic acids such as glucuronic acid. Certain specific compounds of the present disclosure contain both basic and acidic functional groups and thus can be converted to any base or acid addition salts.

The pharmaceutically acceptable salts of the present disclosure can be synthesized from the parent compound containing an acid group or a base by conventional chemical methods. In general, such salts are prepared by reacting these compounds via a free acid or base form with a stoichiometric amount of the appropriate base or acid in water or an organic solvent or a mixture of the two.

In addition to forms of salts thereof, the compounds provided by the present disclosure also exist in forms of prodrug thereof. The prodrugs of the compounds described herein easily chemically transformed under physiological conditions to convert into the compound of the present disclosure. In addition, the prodrug may be converted to the compounds of the present disclosure by chemical or biochemical methods in the in vivo environment.

Certain compounds of the present disclosure may exist in unsolvated or solvated forms, including hydrated forms. Generally, the solvated forms and the unsolvated forms are both included in the scope of the present disclosure.

The compounds of the present disclosure may exist in specific geometric or stereoisomeric forms. The present disclosure contemplates all such compounds, including the cis and trans isomers, the (−)- and (+)-enantiomers, the (R)- and (S)-enantiomers, and the diastereoisomer, a (D)-isomer, a (L)-isomer, and a racemic mixture thereof, and other mixtures such as the mixtures enriched in enantiomer and diastereoisomer, all of which are within the scope of the present disclosure. Additional asymmetric carbon atoms may be present in the substituents such as alkyl groups. All such isomers as well as mixtures thereof are included within the scope of the present disclosure.

Unless otherwise indicated, the term "enantiomer" or "optical isomer" refers to a stereoisomer that is a mirror image of each other.

Unless otherwise indicated, the terms "cis-trans isomer" or "geometric isomer" are caused by the fact that double bonds or single bonds of ring-forming carbon atoms cannot rotate freely.

Unless otherwise indicated, the term "diastereomer" refers to a stereoisomer in which a molecule has two or more chiral centers and a nonmirror image relationship exists between the molecules.

Unless otherwise indicated, "(D)" or "(+)" means dextrorotation, "(L)" or "(−)" means levorotation, "(DL)" or "(±)" means racemization.

Unless otherwise stated, the solid wedge bond () and the wedge dashed bond () represent the absolute configuration of a stereocenter, the straight solid bond () and the straight dashed bond () represent the relative configuration of a stereocenter, the wavy line () represents the solid wedge bond () or the wedge dashed bond (), the wavy line () represents the straight solid bond () and the straight dashed bond ().

The compounds of the present disclosure may be present in particular. Unless otherwise indicated, the terms "tautomer" or "tautomeric form" mean that the different functional isomers are in dynamic equilibrium at room temperature and can be rapidly converted into each other. If tautomers are possible (such as in a solution), the chemical equilibrium of the tautomers can be achieved. For example, proton tautomer (also known as prototropic tautomer) includes interconversions by proton transfer, such as keto-enol isomerization and imine-enamine isomerization. The valence tautomer includes mutual transformation through the recombination of some of the bonding electrons. A specific example of keto-enol tautomerization is the interconversion between two tautomers pentane-2,4-dione and 4-hydroxypent-3-en-2-one.

Unless otherwise indicated, the terms "Being rich in one isomer", "isomer enriched", "being rich in one enantiomer" or "enantiomer enriched" refer to the content of one of the isomers or enantiomers is smaller than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise indicated, the term "isomer excess" or "enantiomeric excess" refers to the relative percentage difference between two isomers or two enantiomers. For example, if one of the isomers or enantiomers is present in an amount of 90% and the other isomer or enantiomer is present in an amount of 10%, the isomer or enantiomeric excess (ee value) is 80%.

The optically active (R)- and (S)-isomers as well as the D and L isomers can be prepared by chiral synthesis or chiral reagents or other conventional techniques. If an enantiomer of the compound of the present disclosure is desired, it can be prepared by asymmetric synthesis or by derivatization with a chiral auxiliary, wherein the resulting mixture of diastereomers is separated and the auxiliary group is cleaved to provide the desired pure enantiomer. Alternatively, when a molecule contains a basic functional group (e.g., an amino group) or an acidic functional group (e.g., a carboxyl group), a diastereomeric salt is formed with a suitable optically active acid or base, and then the diastereomers are resolved by conventional methods well known in the art, and the pure enantiomer is recovered. Furthermore, the separation of enantiomers and diastereomers is generally accomplished by the use of chromatography using a chiral stationary phase optionally combined with chemical derivatization (eg, formation of carbamate from an amine). The compounds of the present disclosure may contain an unnatural proportion of atomic isotopes on one or more of the atoms constituting the compound. For example, a compound can be labeled with a radioisotope such as tritium (3H), iodine-125 ($^{125}$I) or C-14 ($^{14}$C). For another example, the hydrogen can be replaced by heavy hydrogen to form deuterated drugs. The bond formed by deuterium and carbon is stronger than the bond formed by ordinary hydrogen and carbon. Compared with undeuterated drugs, the deuterated drugs have advantages such as reduced toxic and side effects, an increased stability, a strengthen efficacy, and prolonged biological half-life. Alterations of all isotopes of the compounds of the present disclosure, whether radioactive or not, are included within the scope of the present disclosure. The term "pharmaceutically acceptable carrier" refers to any formulation or carrier medium that is capable of delivering an effective amount of an active substance of the present disclosure, does not interfere with the biological activity of the active substance, and has no toxic and side effects on the host or patient, and the representative carrier includes water, oil, vegetables and minerals, cream bases, lotion bases, ointment bases, etc. These bases include suspending agents, tackifiers, transdermal enhancers and the like. Their formulations are well known to those skilled in the cosmetic or topical pharmaceutical arts.

The term "excipient" generally refers to a carrier, a diluent and/or a medium required to prepare an effective pharmaceutical composition.

The term "effective amount" or "therapeutically effective amount", with respect to a pharmaceutical or pharmacologically active agent, refers to a sufficient amount of a drug or agent that is non-toxic but that achieves the desired effect. For oral dosage forms in the present disclosure, an "effective amount" of an active substance in a composition refers to the amount required to achieve the desired effect when used in combination with another active substance in the composition. The determination of the effective amount will vary from person to person, depending on the age and general condition of the recipient, and also depending on the particular active substance, and a suitable effective amount in an individual case can be determined by one skilled in the art based on routine experimentation.

The term "active ingredient", "therapeutic agent", "active substance" or "active agent" refers to a chemical entity that is effective in treating a target disorder, disease or condition.

"Optional" or "optionally" means that the subsequently described event or condition may, but is not necessarily, occur, and the description includes instances in which the event or condition occurs and instances in which the event or condition does not occur.

The term "substituted" means that any one or more hydrogen atoms on a particular atom are replaced by a substituent, and may include variants of heavy hydrogen and hydrogen, as long as the valence of the particular atom is normal and the substituted compound is stable. When the substituent is a keto group (ie, =O), it means that two hydrogen atoms are substituted. Keto substitution does not occur on the aryl group. The term "optionally substituted" means that it may or may not be substituted, and unless otherwise specified, the type and number of substituents may be arbitrary as long as it is chemically achievable.

When any variable (eg, R) occurs one or more times in the composition or structure of a compound, its definition in each case is independent. Thus, for example, if a group is substituted by 0-2 R groups, the group may optionally be substituted at most by two R groups, and R has an independent option in each case. Furthermore, combinations of substituents and/or variants thereof are permissible only if such combinations result in stable compounds.

When the number of one linking group is 0, such as —(CRR)$_0$—, it indicates that the linking group is a single bond.

When one of the variables is selected from a single bond, it means that the two groups to which it is attached are directly linked. For example, when L represents a single bond in A-L-Z, the structure is actually A-Z.

When a substituent is vacant, it means that the substituent is absent. For example, when X is vacant in A-X, the structure is actually A. When the substituents listed do not indicate which atom is attached to the substituted group, such a substituent may be bonded through any atom thereof. For example, as a substituent, pyridyl can be attached to the substituted group through any carbon atom in the pyridine ring.

When the listed linking group does not indicate its attachment direction, its attachment direction is arbitrary. For example, the linking group L in

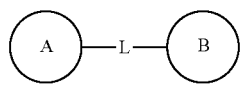

is -M-W-, and at this time -M-W- may connect the ring A and ring B to form

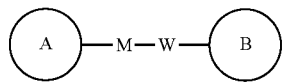

according to the direction the same as the reading direction of from left to right, or -M-W- may connect the ring A and ring B to form

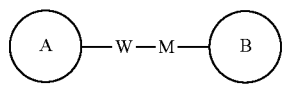

according to the direction opposite to the reading direction of from left to right. The combination of the linking groups, substituents and/or variants thereof is permitted only if such combination produces a stable compound.

Unless otherwise specified, the term "hetero" denotes a heteroatom or a heteroatom group (ie, a radical containing a heteroatom), including atoms other than carbon (C) and hydrogen (H), and radicals containing such heteroatoms, including, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" means a substituted or unsubstituted cycloalkyl, heterocycloalkyl, cycloalkenyl, heterocycloalkenyl, cycloalkynyl, heterocycloalkynyl, aryl, or heteroaryl. The ring includes monocyclic ring, and also includes bicyclic or polycyclic systems, wherein the bicyclic system includes spiro ring, fused ring, and bridge ring. The number of atoms on a ring is usually defined as the number of members of the ring. For example, a "5-7 membered ring" means 5 to 7 atoms are arranged in a circle. Unless otherwise specified, the ring optionally contains 1 to 3 heteroatoms. Thus, the "5-7 membered ring" includes, for example, phenyl, pyridyl, and piperidyl; on the other hand, the term "5-7 membered heterocycloalkyl" includes pyridyl and piperidyl, but does not include phenyl. The term "ring" also includes a ring system containing at least one ring, wherein each "ring" independently conforms to the above definition.

Unless otherwise specified, the term "alkyl" represents a linear or branched saturated hydrocarbon group. In some embodiments, the alkyl is $C_{1-12}$ alkyl; in other embodiments, the alkyl is $C_{1-6}$ alkyl; in other embodiments, the alkyl is $C_{1-3}$ alkyl. The alkyl can be monosubstituted (eg, —CH$_2$F) or polysubstituted (eg, —CF$_3$), and may be monovalent (eg, methyl), divalent (such as methylene) or polyvalent (such as methine). Examples of the alkyl include, but are not limited to, methyl (Me), ethyl (Et), propyl (including n-propyl and isopropyl), butyl (including n-butyl, isobutyl, s-butyl, t-butyl), pentyl (including n-pentyl, isopentyl, neopentyl) and the like.

Unless otherwise specified, the term "alkenyl" represents a linear or branched hydrocarbon group containing one or more carbon-carbon double bonds located at any position of the group. In some embodiments, the alkenyl is $C_{2-8}$ alkenyl; in other embodiments, the alkenyl is $C_{2-6}$ alkenyl; in other embodiments, the alkenyl is $C_{2-4}$ alkenyl. The alkenyl may be monosubstituted or polysubstituted, and may be monovalent, divalent or polyvalent. Examples of the alkenyl include, but are not limited to, vinyl, propenyl, butenyl, pentenyl, hexenyl, butadienyl, piperylene, hexadienyl and the like.

Unless otherwise specified, the term "alkynyl" represents a linear or branched hydrocarbon group containing one or more carbon-carbon triple bonds located at any position of the group. In some embodiments, the alkynyl is $C_{2-8}$ alkynyl; in other embodiments, the alkynyl is $C_{2-6}$ alkynyl; in other embodiments, the alkynyl is $C_{2-4}$ alkynyl. The alkynyl may be monosubstituted or polysubstituted, and may be monovalent, divalent or polyvalent. Examples of the alkynyl include, but are not limited to, ethynyl, propynyl, butynyl, pentynyl and the like.

Unless otherwise specified, the term "heteroalkyl" by itself or in combination with another term refers to a stable linear or branched alkyl radical or a combination thereof having a certain number of carbon atoms and at least one heteroatom or heteroatom group. In some embodiments, the heteroatom is selected from B, O, N, and S, wherein the nitrogen and sulfur atoms are optionally oxidized, and the nitrogen heteroatoms are optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is C$_{1-6}$ heteroalkyl; in other embodiments, the heteroalkyl is C$_{1-3}$ heteroalkyl. The heteroatom or heteroatom group may be located at any internal position of the heteroalkyl, including a position where the alkyl is attached to the rest of the molecule. The terms "alkoxyl", "alkylamino" and "alkylthio" (or thioalkoxy) belong to a customary expression, and refer to those alkyl groups which are attached to the remainder of the molecule through an oxygen atom, an amino group or a sulfur atom, respectively. Examples of the heteroalkyl include, but are not limited to: —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, —CH=CHO—CH$_3$, —CH$_2$—CH=N—OCH$_3$ and —CH=CH—N(CH$_3$)—CH$_3$. At most two heteroatoms can be continuous, such as —CH$_2$—NH—OCH$_3$.

Unless otherwise specified, the term "heteroalkenyl" by itself or in combination with another term refers to a stable linear or branched alkenyl radical or a combination thereof having a certain number of carbon atoms and at least one heteroatom or heteroatom group. In some embodiments, the heteroatom is selected from B, O, N, and S, wherein the nitrogen and sulfur atoms are optionally oxidized, and the nitrogen heteroatoma are optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkenyl is C$_{2-6}$ heteroalkenyl; in other embodiments, the heteroalkyl is C$_{2-4}$ heteroalkenyl. The heteroatom or heteroatom group may be located at any internal position of the heteroalkenyl, including a position where the alkenyl is attached to the rest of the molecule. The terms "alkenyloxy", "alkenylamino" and "alkenylthio" belong to a customary expression, and refer to those alkenyl groups which are attached to the remainder of the molecule through an oxygen atom, an amino group or a sulfur atom, respectively. Examples of the heteroalkenyl include, but are not limited to, —O—CH=CH$_2$, —O—CH=CHCH$_3$, —O—CH=C(CH$_3$)$_2$, —CH=CHO—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. At most two heteroatoms can be continuous, such as —CH=CH—NH—OCH$_3$.

Unless otherwise specified, the term "heteroalkynyl" by itself or in combination with another term refers to a stable linear or branched alkynyl radical or a combination thereof having a certain number of carbon atoms and at least one heteroatom or heteroatom group. In some embodiments, the heteroatom is selected from B, O, N, and S, wherein the nitrogen and sulfur atoms are optionally oxidized, and the nitrogen heteroatom is optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkynyl is C$_{2-6}$ heteroalkynyl; in other embodiments, the heteroalkyl is C$_{2-4}$ heteroalkynyl. The heteroatom or heteroatom group may be located at any internal position of the heteroalkynyl, including a position where the alkynyl is attached to the rest of the molecule. The terms "alkynyloxy", "alkynylamino" and "alkynylthio" belong to a customary expression, and refers to those alkynyl groups which are attached to the remainder of the molecule through an oxygen atom, an amino group, or a sulfur atom, respectively. Examples of the heteroalkynyl include, but are not limited to

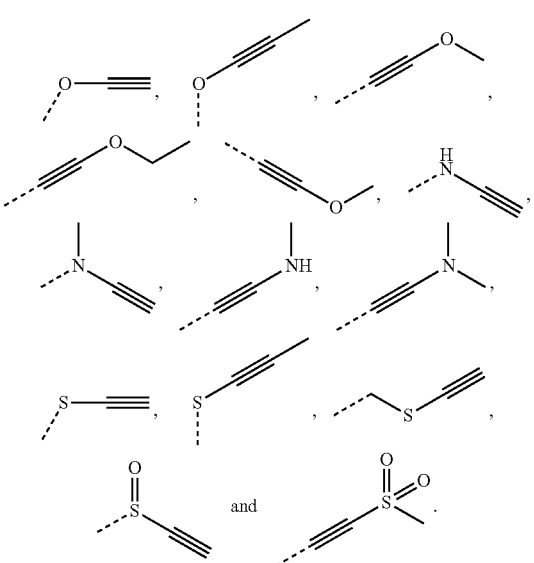

At most two heteroatoms can be continuous, such as

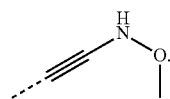

Unless otherwise specified, the term "cycloalkyl" includes any stable cyclic alkyl group, including monocyclic, bicyclic, or tricyclic systems, wherein the bicyclic and tricyclic systems include a spiro ring, a fused ring, and a bridge ring. In some embodiments, the cycloalkyl is C$_{3-8}$ cycloalkyl; in other embodiments, the cycloalkyl is C$_{3-6}$ cycloalkyl; in other embodiments, the cycloalkyl is C$_{5-6}$ cycloalkyl. The cycloalkyl may be monosubstituted or polysubstituted, and may be monovalent, divalent or polyvalent. Examples of these cycloalkyl groups include, but are not limited to, cyclopropyl, cyclobutyl, cyclopentyl, cyclohexyl, cycloheptyl, norbornyl, [2.2.2]bicyclooctane, [4.4.0]bicyclodecane and the like.

Unless otherwise specified, the term "cycloalkenyl" includes any stable cyclic alkenyl group containing one or more unsaturated carbon-carbon double bonds at any position of the group, which includes monocyclic, bicyclic or tricyclic systems, wherein the bicyclic and tricyclic systems include a spiro ring, a fused ring, and a bridge ring, but any ring in this system is non-aromatic. In some embodiments, the cycloalkenyl is C$_{3-8}$ cycloalkenyl; in other embodiments, the cycloalkenyl is C$_{3-6}$ cycloalkenyl; in other embodiments, the cycloalkenyl is $C_{5-6}$ cycloalkenyl. The cycloalkenyl may be monosubstituted or polysubstituted, and may be monovalent, divalent or polyvalent. Examples of these cycloalkenyl groups include, but are not limited to, cyclopentenyl, cyclohexenyl and the like.

Unless otherwise specified, the term "cycloalkynyl" includes any stable cyclic alkynyl group containing one or more carbon-carbon triple bonds at any position of the group, which includes monocyclic, bicyclic or tricyclic systems, wherein the bicyclic and tricyclic systems include a spiro ring, a fused ring, and a bridge ring. It may be monosubstituted or polysubstituted, and may be monovalent, divalent or polyvalent.

Unless otherwise specified, the term "heterocycloalkyl" by itself or in combination with other terms refers to cyclized "heteroalkyl", which includes monocyclic, bicyclic and tricyclic systems, wherein the bicyclic and tricyclic systems include a spiro ring, a fused ring, and a bridge ring. In addition, in the case of the "heterocycloalkyl", a heteroatom may occupy a position where the heterocycloalkyl is bonded to the rest of the molecule. In some embodiments, the heterocycloalkyl is 4-6 membered heterocycloalkyl; in other embodiments, the heterocycloalkyl is 5-6 membered heterocycloalkyl. Examples of the heterocycloalkyl include, but are not limited to, azetidinyl, oxetanyl, thiatanyl, pyrrolidinyl, pyrazolidinyl, imidazolidinyl, tetrahydrothienyl (including tetrahydrothiophene-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl" by itself or in combination with other terms refers to cyclized "heteroalkenyl", which includes monocyclic, bicyclic and tricyclic systems, wherein the bicyclic and tricyclic systems include a spiro ring, a fused ring, and abridge ring, but any ring in this system is non-aromatic. In addition, in the case of the "heterocycloalkenyl", a heteroatom may occupy a position where the heterocycloalkenyl is bonded to the rest of the molecule. In some embodiments, the heterocycloalkenyl is 4-6 membered heterocycloalkenyl; in other embodiments, the heterocycloalkenyl is 5-6 membered heterocycloalkenyl. Examples of heterocycloalkenyl include, but are not limited to,

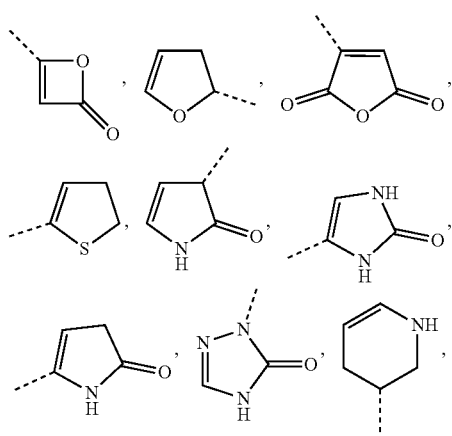

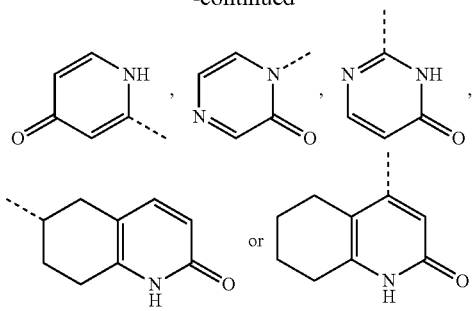

Unless otherwise specified, the term "heterocycloalkynyl" by itself or in combination with other terms refers to a cyclized "heteroalkynyl", which includes monocyclic, bicyclic and tricyclic systems, wherein the bicyclic and tricyclic systems include a spiro ring, a fused ring, and a bridge ring. In addition, in the case of the "heterocycloalkynyl", a heteroatom may occupy a position where the heterocycloalkynyl is bonded to the rest of the molecule. In some embodiments, the heterocycloalkynyl is 4-6 membered heterocycloalkynyl; in other embodiments, the heterocycloalkynyl is 5-6 membered heterocycloalkynyl. Unless otherwise specified, the term "halo" or "halogen", by itself or as a part of another substituent, refers to a fluorine, chlorine, bromine or iodine atom. Further, the term "haloalkyl" is intended to include both monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl, 3-bromopropyl, etc. Unless otherwise specified, examples of haloalkyl include, but are not limited to, trifluoromethyl, trichloromethyl, pentafluoroethyl and pentachloroethyl.

The term "alkoxyl" represents the above alkyl group having a specified number of carbon atoms attached through an oxygen bridge, and unless otherwise specified, $C_{1-6}$ alkoxyl includes $C_1$, $C_2$, $C_3$, $C_4$, $C_5$ and $C_6$ alkoxyl. In some embodiments, the alkoxy is $C_{1-3}$ alkoxy. Examples of alkoxyl include, but are not limited to, methoxy, ethoxy, n-propoxy, isopropoxy, n-butoxy, sec-butoxy, tert-butoxy, n-pentyloxy and S-pentyloxy.

Unless otherwise specified, the terms "aromatic ring" and "aryl" in the present disclosure may be used interchangeably. The term "aromatic ring" or "aryl" refers to a polyunsaturated carbocyclic system, which can be monocyclic, bicyclic or polycyclic system, wherein at least one ring is aromatic, and the rings are fused together in the bicyclic and polycyclic systems. It may be monosubstituted or polysubstituted, and may be monovalent, divalent or polyvalent. In some embodiments, the aryl is $C_{6-12}$ aryl; in other embodiments, the aryl is $C_{6-10}$ aryl. Examples of aryl include, but are not limited to, phenyl, naphthyl (including 1-naphthyl, 2-naphthyl, etc.). The substituent of any one of the above aryl ring systems is selected from the acceptable substituents described in the present disclosure.

Unless otherwise specified, the terms "heteroaryl ring" and "heteroaryl" of the present disclosure may be used interchangeably. The term "heteroaryl" refers to an aryl (or aromatic ring) containing 1, 2, 3 or 4 heteroatom(s) independently selected from B, N, O and S. It may be monocyclic, bicyclic or tricyclic systems, wherein the nitrogen atom may be substituted or unsubstituted (i.e. N or NR, wherein R is H or other substituents as defined herein) and optionally quaternized. The nitrogen and sulfur heteroatoms may be optionally oxidized (i.e. NO and S(O)$_p$, p is 1 or 2).

Heteroaryl may be attached to the remainder of the molecule through heteroatoms. In some embodiments, the heteroaryl is 5-10 membered heteroaryl; in other embodiments, the heteroaryl is 5-6 membered heteroaryl. Examples of the heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazole and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), quinolinyl (including 3-quinolinyl and 6-quinolinyl, etc.), pyrazinyl, purinyl, phenyl and oxazolyl. The substituent of any one of the above heteroaryl ring systems is selected from the acceptable substituents described in the present disclosure.

Unless otherwise specified, the term "aralkyl" is intended to include those groups in which an aryl group is attached to an alkyl group. In some embodiments, the aralkyl is a $C_{6-10}$ aryl-$C_{1-4}$ alkyl; in other embodiments, the aralkyl is $C_{6-10}$ aryl-$C_{1-2}$ alkyl. Examples of the aralkyl include, but are not limited to, benzyl, phenethyl, menaphthyl and the like. The terms "aryloxy" and "arylthio" represent those groups in which the carbon atom (such as methyl) in the aralkyl has been replaced by an oxygen or sulfur atom. In some embodiments, the aryloxy is $C_{6-10}$ aryl-O—$C_{1-2}$ alkyl; in other embodiments, the aryloxy is $C_{6-10}$ aryl-$C_{1-2}$ alkyl-O—. In some embodiments, the arylthio is $C_{6-10}$ aryl-S—$C_{1-2}$ alkyl; in other embodiments, the arylthio is $C_{6-10}$ aryl-$C_{1-2}$ alkyl-S—. Examples of aryloxy and arylthio include, but are not limited to, phenoxymethyl, 3-(1-naphthyloxy) propyl, phenylthiomethyl and the like.

Unless otherwise specified, the term "heteroaralkyl" is intended to include those groups in which a heteroaryl group is attached to an alkyl group. In some embodiments, the heteroaralkyl is 5-8 membered heteroaryl-$C_{1-4}$ alkyl; in other embodiments, the heteroaralkyl is 5-6 membered heteroaryl-$C_{1-2}$ alkyl. Examples of heteroaralkyl include, but are not limited to, pyrrolylmethyl, pyrazolylmethyl, pyridylmethyl, pyrimidinylmethyl and the like. The terms "heteroaryloxy" and "heteroarylthio" respectively refer to those groups in which a carbon atom (such as methyl) in the heteroaralkyl group have been replaced by an oxygen or sulfur atom. In some embodiments, the heteroaryloxy is 5-8 membered heteroaryl-O—$C_{1-2}$ alkyl; in other embodiments, the heteroaryloxy is 5-6 membered heteroaryl-$C_{1-2}$ alkyl-O—. In some embodiments, the heteroarylthio is 5-8 membered heteroaryl-S—$C_{1-2}$ alkyl; in other embodiments, the heteroarylthio is 5-6 membered heteroaryl-$C_{1-2}$ alkyl-S—. Examples of heteroaryloxy and heteroarylthio include, but are not limited to, pyrroleoxymethyl, pyrazolyloxymethyl, 2-pyridyloxymethyl, pyrrolylthiomethyl, pyrazolylthiomethyl, 2-pyridylthiomethyl and the like.

Unless otherwise specified, $C_{n-n+m}$ or $C_n$-$C_{n+m}$ includes cases where the carbon number is a specific number from n to n+m, and also includes cases wherein the carbon number is in a range within n to n+m. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n to n+m membered ring means that the number of atoms in the ring is from n to n+m, or the number of atoms is in any range from n to n+m. For example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring, and also includes 3-6 membered ring, 3-9 membered ring, 5-6 membered ring, 5-7 membered ring, 6-7 membered ring, 6-8 membered ring, and 6-10 membered ring.

The term "leaving group" refers to a functional group or atom which may be substituted by another functional group or atom by a substitution reaction (for example, a nucleophilic substitution reaction). For example, representative leaving groups include triflate; chlorine, bromine, and iodine; sulfonate groups such as methanesulfonate, tosylate, p-bromobenzene sulfonate, p-tosylate and the like; acyloxy such as acetoxyl, trifluoroacetoxyl and the like.

The term "protecting group" includes but is not limited to "amino protecting group", "hydroxy protecting group" or "mercapto protecting group". The term "amino protecting group" refers to a protecting group suitable for preventing side reactions at the nitrogen position of the amino group. Representative amino protecting groups include, but are not limited to, formyl, acyl such as alkanoyl (such as acetyl, trichloroacetyl, or trifluoroacetyl), alkoxycarbonyl such as t-butoxycarbonyl (Boc), arylmethoxycarbonyl such as carbobenzoxy (Cbz) and 9-fluorenylmethoxycarbonyl (Fmoc), arylmethyl such as benzyl (Bn), trityl (Tr), 1,1-di-(4'-methoxyphenyl) methyl, and silyl such as trimethylsilyl (TMS) and t-butyldimethylsilyl (TBS), etc. The term "hydroxyl protecting group" refers to a protecting group suitable for preventing side reactions of hydroxyl groups. Representative hydroxy protecting groups include, but are not limited to, alkyl such as methyl, ethyl, and t-butyl, acyl such as alkanoyl (such as acetyl), arylmethyl such as benzyl (Bn), p-methyl Oxybenzyl (PMB), 9-fluorenylmethyl (Fm) and diphenylmethyl (diphenylmethyl, DPM), and silyl such as trimethylsilyl (TMS) and t-butyldimethylsilyl (TBS), etc.

The compounds of the present disclosure may be prepared by a variety of synthetic methods well known to those skilled in the art, including the specific embodiments set forth below, embodiments formed through combinations thereof with other chemical synthetic methods, and those equivalent alternatives well known to those skilled in the art, and preferred embodiments include, but are not limited to, embodiments of the present disclosure.

The compounds of the present disclosure can have various applications or can be used to treat various diseases, including but not limited to the specific applications or diseases listed herein.

The solvent used in the present disclosure is commercially available. The present disclosure employs the following abbreviations: aq stands for water; HATU stands for O-(7-azabenzotriazol-1-yl)-N,N,N',N'-tetramethyl urea hexafluorophosphate; EDC stands for N-(3-dimethylaminopropyl)-N'-ethylcarbodiimide hydrochloride; m-CPBA stands for 3-chloroperoxybenzoic acid; eq stands for equivalent weight, and equal weight; CDI stands for carbonyl diimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc represents ethyl acetate; EtOH represents ethanol; MeOH represents methanol; CBz represents benzyloxycarbonyl, an amine protecting group; BOC represents t-butoxycarbonyl which is an amine protecting group; HOAc represents acetic acid; $NaCNBH_3$ represents sodium cyanoborohydride; r.t. represents room temperature; O/N stands for overnight; THF stands for tetrahydrofuran; $Boc_2O$ stands for di-tert-butyldicarbonate; TFA stands for trifluoroacetic acid; DIPEA stands for diisopropylethylamine; $SOCl_2$ stands for thionyl chloride; $CS_2$ stands for carbon disulfide; TsOH stands for p-toluenesulfonic acid; NFSI stands for N-fluoro-N-(phenylsulfonyl)benzenesulfonamide; NCS stands for N-chlorosuccinimide; n-$Bu_4NF$ stands for tetrabutylammonium fluoride; iPrOH stands for 2-propanol; mp stands for melting point; LDA stands for lithium diisopropylamide; and NMP stands for N-methyl pyrrolidone.

Compounds are named by hand or by ChemDraw® software, and commercial compounds are based on supplier catalog names.

DETAILED DESCRIPTION

Figure 1:
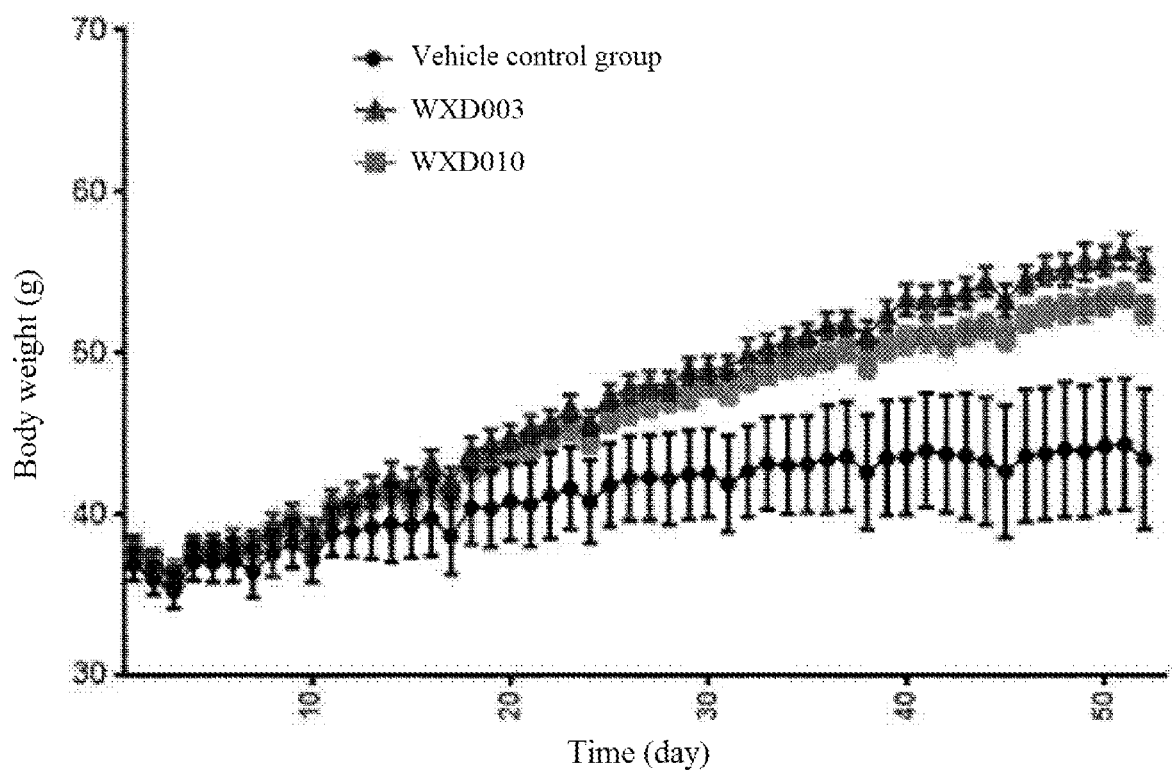
FIG. 1: Results of changes in the body weight of animal from week 1 to week 8.

The present disclosure is described in detail below by referring to the examples, which are not intended to adversely limit the present disclosure. The present disclosure has been described in detail herein, the embodiments of the present disclosure are disclosed herein, and various modifications and changes may be made to the embodiments of the present disclosure without departing from the spirit and scope of the present disclosure, which is obvious for those skilled in the art.

Reference Example 1: Fragment A-1

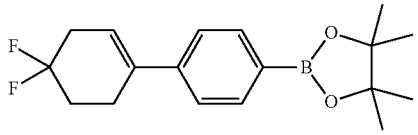 [SMILES: CC1(C)OB(c2ccc(C3=CCC(F)(F)CC3)cc2)OC1(C)C]

Synthesis Route:

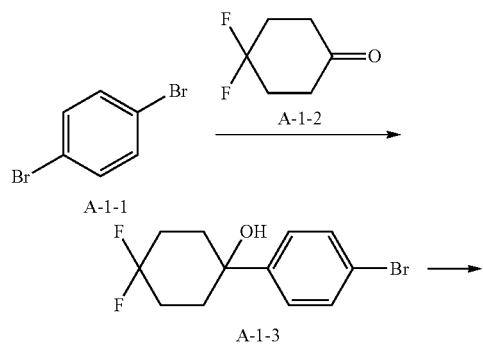

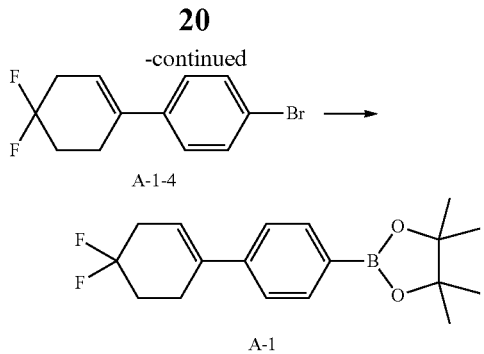

Compound A-1-1 (20 g, 84.78 mmol, 10.87 mL, 1 eq) and tetrahydrofuran (125 mL) were successively added to a pre-dried three-necked flask (500 mL). After replaced with nitrogen, the flask was cooled to −78° C., and N-butyl-lithium (2.5 M, 37.64 mL, 1.11 eq) was slowly added dropwise thereto, and then stirring was performed for 0.5 hours. Finally, compound A-1-2 (12.5 g, 93.26 mmol, 1.1 eq) was added to the flask, and then the temperature was slowly raised to 0° C., and stirring was performed for 0.5 hours. After the reaction was completed, the resulted reaction solution was slowly quenched with a saturated aqueous solution of ammonium chloride (200 mL) at 0-10° C. Then the reaction solution was extracted with ethyl acetate (200 mL×2) to obtain organic phases. The combined organic phases were washed with saturated sodium chloride (100 mL), dried with anhydrous sodium sulfate desiccant, filtered to remove the desiccant, and concentrated in vacuo to remove the solvent, obtaining a crude compound A-1-3, which was directly used in the next reaction without purification.

Step 2: Synthesis of Compound A-1-4.

Compound A-1-3 (23.2 g, 79.82 mmol, 1 eq) and toluene (600 mL) were successively added to a pre-dried three-necked flask (1000 mL), and then p-toluenesulfonic acid monohydrate (1.82 g, 9.58 mmol, 0.12 eq) was added thereto. After replaced with nitrogen, the flask was heated to 130° C., and stirring was performed for 10 hours (equipped with Dean-Stark). After the reaction was completed, the reaction solution was cooled down, and concentrated in vacuo to remove the solvent to obtain a residue. The residue was subjected to column chromatography (petroleum ether/ethyl acetate system) to separate compound A-1-4. $^1H$ NMR (400 MHz, CHLOROFORM-d) δ: 7.49-7.43 (m, 2H), 7.27-7.22 (m, 2H), 5.91 (dt, J=1.3, 2.6 Hz, 1H), 2.80-2.63 (m, 4H), 2.19 (tt, J=6.7, 13.7 Hz, 2H).

Step 3: Synthesis of Compound A-1.

Compound A-1-4 (2.9 g, 10.62 mmol, 1 eq), pinacol borate (5.39 g, 21.24 mmol, 2 eq), potassium acetate (3.13 g, 31.85 mmol, 3 eq) and 1,4-dioxane (30 mL) were successively added to a pre-dried one-necked 100 mL flask. After replaced with nitrogen, 1,1'-bis(diphenylphosphino)ferrocene palladium chloride (776.94 mg, 1.06 mmol, 0.1 eq) was added into the reaction. After replaced with nitrogen again, the flask was heated to 70° C. and stirring was performed for 10 hours. After the reaction was completed, the reaction was cooled down and concentrated in vacuo to remove the solvent to obtain a residue. The residue was purified by column chromatography (petroleum ether/ethyl acetate system) to obtain compound A-1. $^1H$ NMR (400 MHz, CHLOROFORM-d) δ: 7.78 (d, J=8.4 Hz, 2H), 7.38 (d, J=8.2 Hz, 2H), 5.97 (br s, 1H), 2.79-2.66 (m, 4H), 2.19 (tt, J=6.6, 13.7 Hz, 2H), 1.36 (s, 12H).

The fragments A2-8 in the following table are synthesized with reference to the steps 1-3 as described in the Reference Example 1. The structures in the table also include their possible isomers.

| Reference Example | Fragments A | Structure | ¹H NMR |
|---|---|---|---|
| 2 | A-2 | 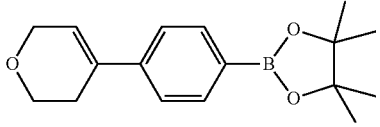 [SMILES: CC1(C)OB(c2ccc(C3=CCOCC3)cc2)OC1(C)C] | ¹H NMR (400 MHz, CHLOROFORM-d) δ ppm 1.35 (s, 12H), 2.49-2.60 (m, 2H), 3.94 (t, J = 5.40 Hz, 2H), 4.33 (q, J = 2.76 Hz, 2H), 6.19 (dt, J = 2.82, 1.47 Hz, 1H), 7.40 (d, J = 8.03 Hz, 2H), 7.76-7.81 (m, 2H) |
| 3 | A-3 | 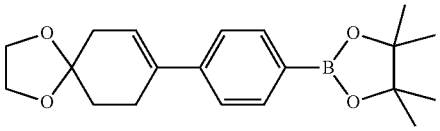 [SMILES: CC1(C)OB(c2ccc(C3=CCC4(CC3)OCCO4)cc2)OC1(C)C] | ¹H NMR (400 MHz, CHLOROFORM-d) δ ppm 7.75 (d, J = 8.3 Hz, 2H), 7.40 (d, J = 8.0 Hz, 2H), 6.03-6.07 (m, 1H), 4.03 (s, 4H), 2.64-2.72 (m, 2H), 2.48 (br d, J = 1.3 Hz, 2H), 1.93 (t, J = 6.4 Hz, 2H), 1.35 (s, 12H) |
| 4 | A-4 | 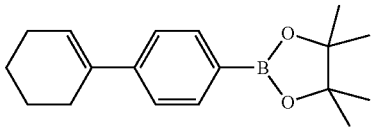 | ¹H NMR (400 MHz, CHLOROFORM-d) δ ppm 1.35 (s, 12H), 1.62-1.72 (m, 2H), 1.74-1.85 (m, 2H), 2.18-2.26 (m, 2H), 2.37-2.46 (m, 2H), 6.19 (dt, J = 3.76, 2.13 Hz, 1H), 7.39 (d, J = 8.28 Hz, 2H), 7.76 (d, J = 8.03 Hz, 2H) |
| 5 | A-5 | 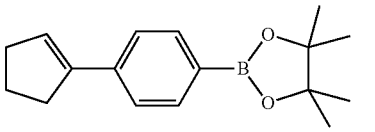 [SMILES: CC1(C)OB(c2ccc(C3=CCCC3)cc2)OC1(C)C] | ¹H NMR (400 MHz, CHLOROFORM-d) δ ppm 7.75 (d, J = 8.1 Hz, 2H), 7.43 (d, J=8.1 Hz, 2H), 6.26 (t, J = 1.9 Hz, 1H), 2.68-2.76 (m, 2H), 2.54 (td, J = 7.4, 2.4 Hz, 2H), 1.98-2.05 (m, 2H), 1.35 (s, 12H) |
| 6 | A-6 | 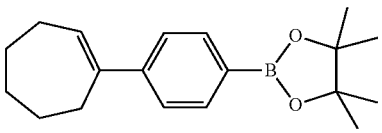 [SMILES: CC1(C)OB(c2ccc(C3=CCCCCC3)cc2)OC1(C)C] | ¹H NMR (400 MHz, CHLOROFORM-d) δ ppm 7.74 (d, J = 8.0 Hz, 2 H), 7.32 (d, J = 8.0 Hz, 2H), 6.14 (t, J = 6.8 Hz, 1H), 2.57-2.66 (m, 2H), 2.27-2.33 (m, 2H), 1.81-1.87 (m, 2H), 1.65 (dt, J = 11.0, 5.6 Hz, 2H), 1.57 (s, 2H), 1.34-1.36 (m, 12H) |
| 7 | A-7 | 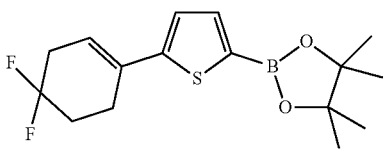 [SMILES: CC1(C)OB(c2ccc(C3=CCC(F)(F)CC3)s2)OC1(C)C] | ¹H NMR (400 MHz, CHLOROFORM-d) δ ppm 7.43 (d, J = 3.5 Hz, 1H), 6.98-7.00 (m, 1H), 6.00 (br s, 1H , 2.79-2.69 (m, 4H), 2.03-2.18 (m, 2H), 1.27 (s, 12H) |
| 8 | A-8 | 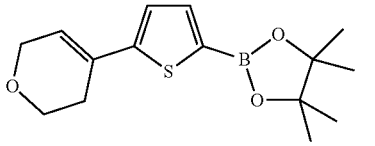 [SMILES: CC1(C)OB(c2ccc(C3=CCOCC3)s2)OC1(C)C] | ¹H NMR (400 MHz, CHLOROFORM-d) δ ppm 1.35 (s, 12H), 2.46-2.64 (m, 2H), 3.92 (t, J = 5.52 Hz, 2H), 4.30 (q, J = 2.76 Hz, 2H), 6.21 (dt, J = 3.01, 1.51 Hz, 1H), 7.07 (d, J = 3.51 Hz, 1H), 7.52 (d, J = 3.51 Hz, 1H) |

Reference Example 9: Fragment B-1

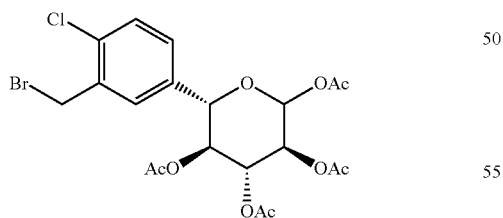

Synthesis Route:

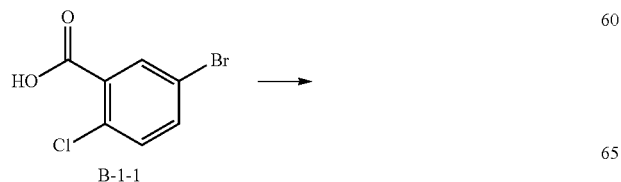

-continued

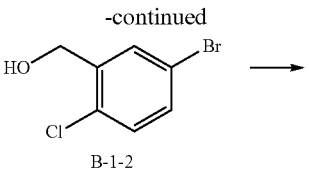

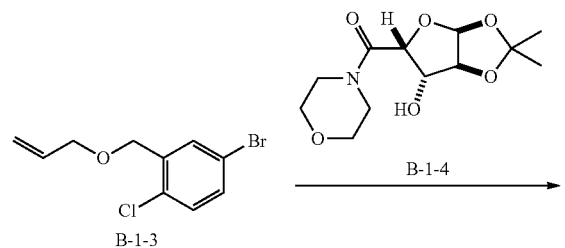

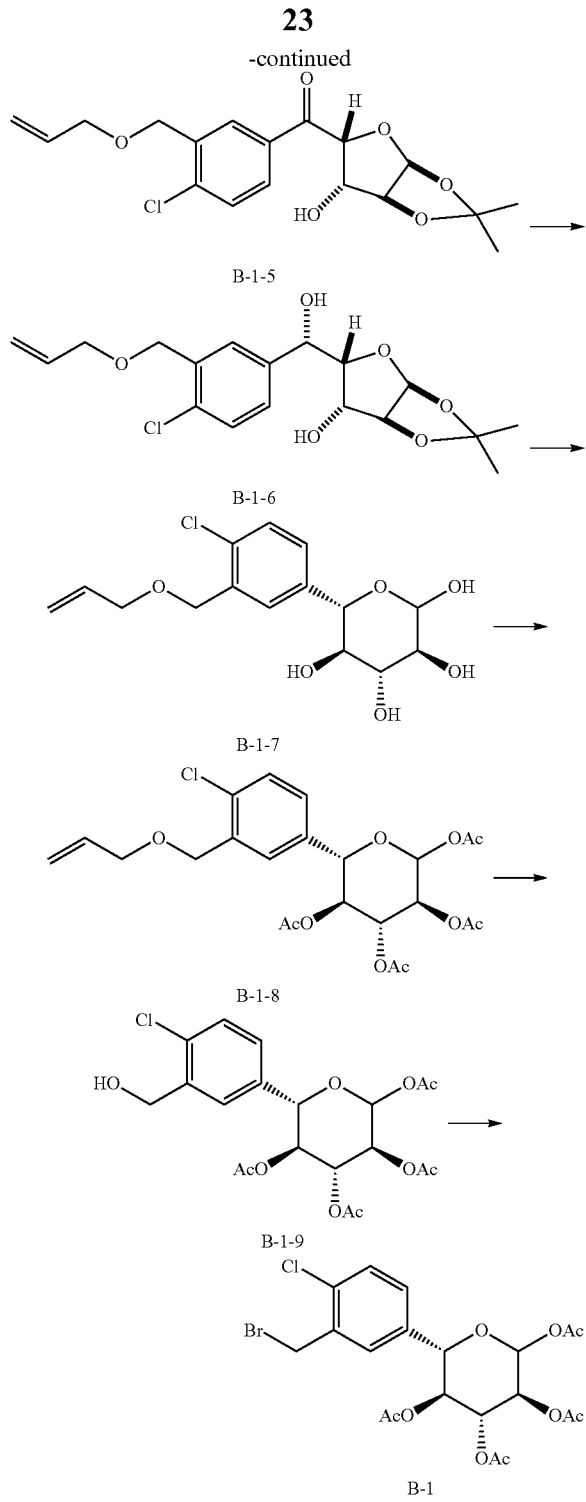

Step 1: Synthesis of Compound B-1-2

Compound B-1-1 (30 g, 127.41 mmol, 1 eq) and tetrahydrofuran (6 mL) were added to a 3 L three-necked flask, and the borane tetrahydrofuran complex (1 M, 382.23 mL, 3 eq) was added thereto under blowing nitrogen protection. The resulted mixture was reacted at 25° C. for 16 hours. After the reaction was completed, the resulted reaction solution was quenched by dropwise addition with methanol (150 mL) at 25° C. under blowing nitrogen protection. Then the reaction solution was concentrated in vacuo at 45° C. with a water pump to obtain compound B-1-2. $^1$H NMR (400 MHz, CHLOROFORM-d) δ=7.68 (d, J=2.4 Hz, 1H), 7.37 (dd, J=2.2, 8.6 Hz, 1H), 7.22 (d, J=8.4 Hz, 1H), 4.77 (d, J=5.3 Hz, 2H).

Step 2: Synthesis of Compound B-1-3.

Compound B-1-2 (27 g, 121.91 mmol, 1 eq) and dimethylformamide (150 mL) were added to a three-necked flask. After protected with nitrogen, sodium hydride (9.75 g, 243.82 mmol, 60% purity, 2 eq) was added thereto at 0° C. Half an hour later, allyl bromide (44.24 g, 365.73 mmol, 32.06 mL, 3 eq) was added thereto, and the resulted mixture was reacted at 25° C. for 15.5 hours. After the reaction was completed, the resulted reaction solution was quenched with a saturated aqueous solution of ammonium chloride (500 mL), and extracted with dichloromethane (100 mL×3). The organic phases were washed with a saturated saline solution (500 mL), dried with anhydrous sodium sulfate, and filtered to collect a filtrate. The filtrate was concentrated in vacuo at 45° C. with a water pump, obtaining a crude product. The crude product was purified by passing a rapid column (SiO$_2$—, 100-200 mesh, PE:EA=1:0 to 10:1) to obtain compound B-1-3. H NMR (400 MHz, CHLOROFORM-d) δ=7.67 (d, J=2.4 Hz, 1H), 7.35 (dd, J=2.4, 8.4 Hz, 1H), 7.21 (d, J=8.4 Hz, 1H), 6.08-5.91 (m, 1H), 5.39 (q, J=1.6 Hz, 1H), 5.34 (q, J=1.5 Hz, 1H), 5.29-5.24 (q, 1H), 4.57 (s, 2H), 4.13 (td, J=1.3, 5.6 Hz, 2H).

Step 3: Synthesis of Compound B-1-5.

Compound B-1-4 (9.9 g, 36.23 mmol, 1 eq) and THF (70.5 mL) were added to a three-necked flask. After replaced with nitrogen, the flask was cooled to 0° C., and tert-butyl Grignard reagent (2M, 29.70 mL, 1.64 eq) was added thereto, and the resulted mixture was reacted at 0° C. for 1 hour to obtain a first reaction solution. Compound B-1-3 (12.32 g, 47.09 mmol, 1.3 eq) and tetrahydrofuran (141 mL) were added to a three-necked flask. After replaced with nitrogen, the flask was cooled to −78° C., and N-butyl lithium (2.5M, 21.74 mL, 1.5 eq) was added thereto, and the resulted mixture was reacted at −78° C. for 0.5 hours to obtain a second reaction solution. The first reaction solution was then added dropwise to the second reaction solution using a syringe to perform reaction at −78° C. for 1 hour and then at 25° C. for 13.5 hours. After the reaction was completed, the resulted reaction solution was quenched with a saturated aqueous solution of ammonium chloride (400 mL), then extracted with ethyl acetate (100 mL×3). The organic phases were washed with a saturated saline solution (1000 mL), dried with anhydrous sodium sulfate, and filtered to collect a filtrate. The filtrate was concentrated in vacuo at 45° C. by reducing pressure with a water pump to obtain a crude product. The crude product was purified by passing a rapid column (petroleum ether/ethyl acetate system) to obtain compound B-1-5. $^1$H NMR (400 MHz, CHLOROFORM-d) β=8.21 (s, 1H), 7.94 (dd, J=2.0, 8.4 Hz, 1H), 7.48 (d, J=8.2 Hz, 1H), 6.10 (d, J=3.5 Hz, 1H), 6.05-5.94 (m, 1H), 5.38 (dd, J=1.5, 17.2 Hz, 1H), 5.33 (d, J=2.6 Hz, 1H), 5.28-5.23 (m, 1H), 4.65 (s, 2H), 4.63 (br d, J=3.3 Hz, 1H), 4.61 (d, J=3.5 Hz, 1H), 4.15 (d, J=5.5 Hz, 2H), 2.97 (d, J=4.2 Hz, 1H), 1.59 (s, 3H), 1.38 (s, 3H).

Step 4: Synthesis of Compound B-1-6.

Compound B-1-5 (8 g, 21.69 mmol, 1 eq), cerium chloride heptahydrate (9.70 g, 26.03 mmol, 2.47 mL, 1.2 eq) and methanol (180 mL) were added to a reaction flask. After replaced with nitrogen, sodium borohydride (1.64 g, 43.38 mmol, 2 eq) was added thereto at 0° C., and the resulted mixture was reacted at 25° C. for 16 hours. After the reaction was completed, the reaction solution was quenched with a saturated aqueous solution of ammonium chloride (250 mL), and a saturated saline solution (250 mL) was added thereto.

Then, the reaction solution was extracted with ethyl acetate (100 mL×3) to obtain organic phases (if the liquid is difficult to separate during extraction, the liquid can be separated by filtration with diatomite). The organic phases were dried by anhydrous sodium sulfate and filtered to collect a filtrate. The filtrate was concentrated to dry at 45° C. by reducing pressure with a water pump to obtain compound B-1-6. $^1$H NMR (400 MHz, CHLOROFORM-d) δ=7.61-7.56 (m, 1H), 7.42-7.31 (m, 2H), 6.05-5.92 (m, 2H), 5.41-5.32 (m, 1H), 5.28-5.18 (m, 2H), 4.64-4.59 (m, 2H), 4.49 (d, J=3.5 Hz, 1H), 4.16-4.03 (m, 5H), 3.36 (br s, 1H), 1.46 (s, 3H), 1.30 (s, 3H).

Step 5: Synthesis of Compound B-1-7.

Compound B-1-6 (7.2 g, 19.42 mmol, 1 eq), water (45 mL) and acetic acid (44.31 g, 737.82 mmol, 42.20 mL, 38 eq) were added into a reaction flask to perform reaction at 100° C. for 7 hours. After the reaction was completed, the reaction solution was concentrated to dry at 45° C. by reducing pressure with a water pump, and then subjected to azeotropic drying with toluene (100 mL×2), obtaining compound B-1-7. $^1$H NMR (400 MHz, CHLOROFORM-d) δ=7.42 (br d, J=8.6 Hz, 1H), 7.18 (br s, 1H), 7.09 (br d, J=6.8 Hz, 1H), 5.80 (tt, J=6.0, 16.8 Hz, 1H), 5.54-5.08 (m, 4H), 4.58 (br d, J=5.3 Hz, 1H), 4.43 (br s, 2H), 4.08 (br s, 1H), 4.14-3.80 (m, 3H), 3.62-3.28 (m, 3H), 2.20 (br s, 1H).

Step 6: Synthesis of Compound B-1-8.

Compound B-1-7 (6 g, 18.14 mmol, 1 eq), triethylamine (12.11 g, 119.72 mmol, 16.66 mL, 6.6 eq) and acetonitrile (110 mL) were added into a single-necked flask, and then acetic anhydride (12.22 g, 119.72 mmol, 11.21 mL, 6.6 eq) and dimethylaminopyridine (22.16 mg, 181.40 umol, 0.01 eq) were successively added thereto to perform reaction at 25° C. for 16 hours. After the reaction was completed, the reaction solution was quenched with a saturated aqueous solution of sodium bisulfate (100 mL), extracted with ethyl acetate (50 mL×3). The organic phases were washed with a saturated saline solution (200 mL), dried with anhydrous sodium sulfate and filtered to collect a filtrate. The filtrate was concentrated to dry at 45° C. by reducing pressure with a water pump to obtain a crude product. The crude product was purified by passing a rapid column (petroleum ether/ethyl acetate system) to obtain compound B-1-8. $^1$H NMR (400 MHz, CHLOROFORM-d) δ=7.49 (d, J=1.9 Hz, 1H), 7.33 (d, J=8.3 Hz, 1H), 7.25-7.21 (dd, 1H), 5.99 (tdd, J=5.6, 10.4, 17.2 Hz, 1H), 5.87 (d, J=8.3 Hz, 1H), 5.41-5.36 (m, 1H), 5.36-5.31 (m, 1H), 5.30-5.23 (m, 2H), 5.17-5.10 (t, 1H), 4.61-4.52 (m, 3H), 4.12-4.08 (m, 2H), 2.13-2.10 (s, 3H), 2.07 (s, 3H), 2.04-1.99 (s, 3H), 1.85 (s, 3H).

Step 7: Synthesis of Compound B-1-9.

Compound B-1-8 (6.5 g, 13.03 mmol, 1 eq), sodium acetate (4.28 g, 52.11 mmol, 4 eq), water (13 mL) and glacial acetic acid (117 mL) were added to a reaction flask. The reaction was cooled to 5° C. after replaced with nitrogen, and palladium dichloride (5.08 g, 28.66 mmol, 2.2 eq) was added thereto. The resulted mixture was reacted at 25° C. for 16 hours. After the reaction was completed, the reaction solution was concentrated to dry at 45° C. by reducing pressure with a water pump to obtain a crude product. The crude product was purified by passing a rapid column (petroleum ether/ethyl acetate system) to obtain compound B-1-9. H NMR (400 MHz, CHLOROFORM-d) δ=7.53 (d, J=1.8 Hz, 1H), 7.33 (d, J=8.2 Hz, 1H), 7.21 (dd, J=2.1, 8.3 Hz, 1H), 5.87 (d, J=8.2 Hz, 1H), 5.41-5.34 (t, 1H), 5.30-5.23 (t, 1H), 5.15 (t, J=9.6 Hz, 1H), 4.77 (br d, J=2.4 Hz, 2H), 4.56 (d, J=9.9 Hz, 1H), 2.15-2.10 (s, 3H), 2.07 (s, 3H), 2.02 (s, 3H), 1.85 (s, 3H).

Step 8: Synthesis of Compound B-1.

Compound B-1-9 (1 g, 2.18 mmol, 14.04 μL, 1 eq), triphenylphosphine (857.44 mg, 3.27 mmol, 1.5 eq) and dichloromethane (20 mL) were added to a reaction flask, and stirred for half an hour after protected with nitrogen, and then N-bromosuccinimide (581.85 mg, 3.27 mmol, 1.5 eq) was added thereto at 0° C. The resulted mixture was reacted at 25° C. for 15.5 hours. After the reaction was completed, the reaction solution was concentrated to dry at 25° C. to obtain a crude product. The crude product was purified by passing a rapid column (petroleum ether/ethyl acetate system) to obtain compound B-1. $^1$H NMR (400 MHz, CHLOROFORM-d) δ=7.44-7.36 (m, 2H), 7.29 (s, 1H), 5.87 (d, J=8.2 Hz, 1H), 5.41-5.34 (t, 1H), 5.30-5.23 (m, 1H), 5.15-5.03 (m, 1H), 4.68-4.59 (d, 1H), 4.53 (t, J=9.9 Hz, 2H), 2.22 (s, 1H), 2.13 (s, 2H), 2.08-2.05 (m, 3H), 2.04-2.01 (m, 3H), 1.91-1.86 (m, 3H).

Reference Example 10: Fragment B-2

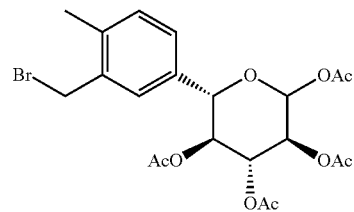 [SMILES: CC(=O)OC1O[C@@H](c2ccc(C)c(CBr)c2)[C@H](OC(C)=O)[C@@H](OC(C)=O)[C@@H]1OC(C)=O]

Synthesis Route:

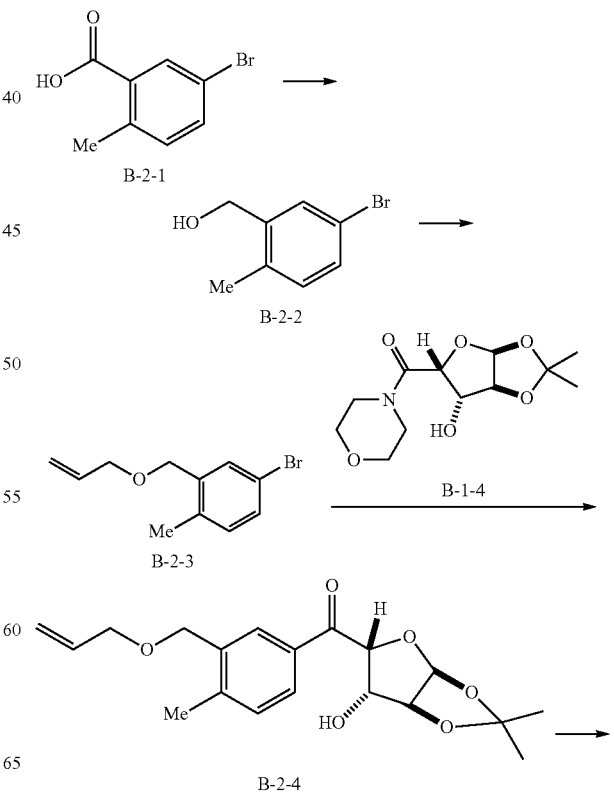

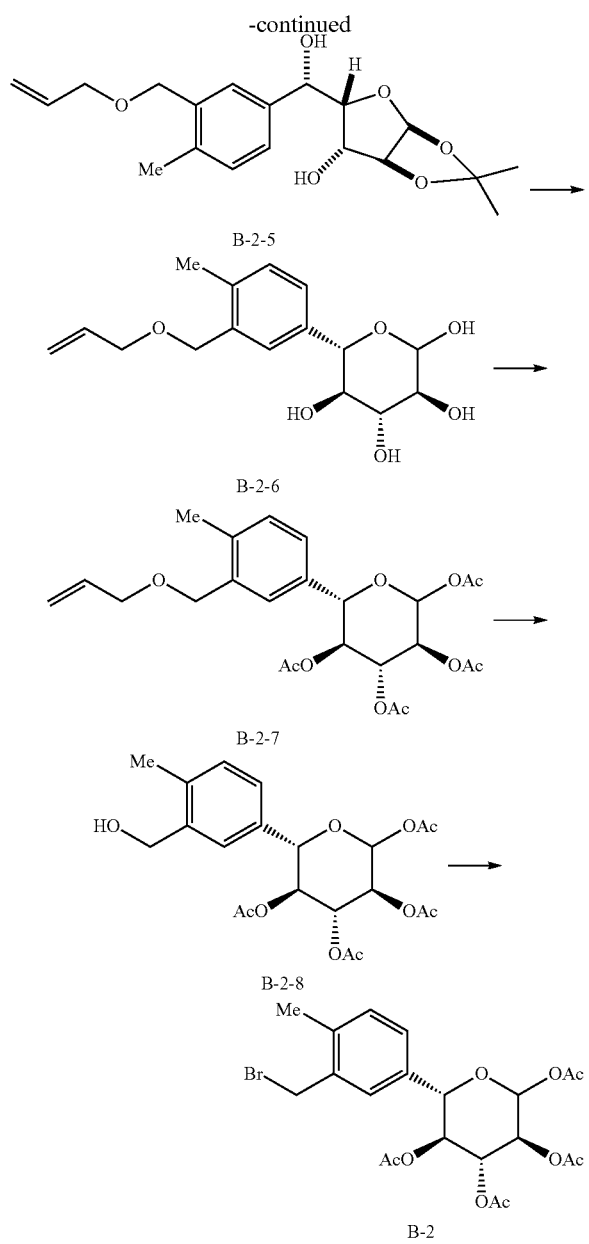

Step 1: Synthesis of Compound B-2-2

Lithium aluminum hydride (11 g, 289.82 mmol, 1.25 eq) was dissolved in tetrahydrofuran (200 mL) at 0° C., and filled with nitrogen protection after replaced with nitrogen three times. Compound B-2-1 (50 g, 232.51 mmol, 1 eq) was dissolved in tetrahydrofuran (200 mL), and the resulted solution was slowly added to the reaction solution at 0° C. Bubbles were observed and the reaction solution was heated to 25° C. to continue reaction for 2 hours. Water (11 mL) was slowly added dropwise thereto at 0° C., then 15% aqueous solution of sodium hydroxide (11 mL) was added thereto, and finally water (33 mL) was added thereto. The resulted mixture was filtered to obtain a residue which was then washed twice with ethyl acetate, and the filtrate was concentrated in vacuo to obtain a crude compound B-2-2.

Step 2: Synthesis of Compound B-2-3

Compound B-2-2 (47.9 g, 238.24 mmol, 1 eq) was dissolved in dimethylformamide (120 mL), and sodium hydride (14.29 g, 357.36 mmol, 60% purity, 1.5 eq) was added thereto at 0° C. Stirring was performed at 25° C. for 0.5 hours, and then 3-bromopropene (57.64 g, 476.47 mmol, 41.17 mL, 2 eq) was slowly added to the reaction solution to continue the reaction at 25° C. for 2 hours. After the reaction was completed, the reaction solution was quenched with water (50 mL) at 0° C., extracted with ethyl acetate (500 mL×2), washed with water (50 mL×2) and then washed with a saturated saline solution (50 mL×2), and dried with anhydrous sodium sulfate to obtain a crude product. The crude product was purified by column chromatography (petroleum ether/ethyl acetate system) to obtain the target compound B-2-3.

Step 3: Synthesis of Compound B-2-4

Compound B-2-3 (18.5 g, 76.72 mmol, 1.2 eq) was dissolved in tetrahydrofuran (100 mL) at −78° C., and then n-butyllithium (2.5 M, 33.25 mL, 1.3 eq) was added under nitrogen protection to perform reaction at −78° C. for 0.5 hours, obtaining alkyl lithium solution. Compound B-1-4 (17.47 g, 63.93 mmol, 1 eq) was dissolved in tetrahydrofuran (100 mL), cooled to 0° C. and tert-butyl magnesium chloride (1.7 M, 41.37 mL, 1.1 eq) was added dropwise under nitrogen protection to perform reaction at 0° C. for 0.5 hours, obtaining a magnesium alkoxy solution. The magnesium alkoxy solution was slowly added to the alkyl lithium solution at −78° C. to perform reaction at −78° C. for 0.5 hours, then the temperature was raised to 25° C. to continue reaction for 15.5 hours. After the reaction was completed, an amine chloride solution (50 mL) was added to the resulted reaction solution at 0° C. and ethyl acetate (200 mL) was added to dilute the reaction solution. Then the reaction solution was washed with water (50 mL×2) to obtain organic phases. The combined organic phases were washed with saturated saline solution (50 mL×2) to remove the residue water. Then the resulted was dried with anhydrous sodium sulfate, filtered and dried by rotation to obtain a crude product. The crude product was purified by column chromatography (petroleum ether/ethyl acetate system) to obtain the target compound B-2-4.

Step 4: Synthesis of Compound B-2-5

Compound B-2-4 (17.80 g, 51.09 mmol, 1 eq) was dissolved in methanol (100 mL), cooled to 0° C., and cerium trichloride heptahydrate (22.84 g, 61.31 mmol, 5.83 mL, 1.2 eq) and sodium borohydride (3.87 g, 102.18 mmol, 2 eq) were added thereto successively, raised to 25° C. to perform reaction for 16 hours. After the reaction was completed, the resulted reaction solution was quenched with water (30 mL) and concentrated in vacuo. Then the resulted was diluted with ethyl acetate (100 mL) and washed with water (50 mL×2). Water was removed by using a saturated saline solution (50 mL×2). Finally, the solution was dried with anhydrous sodium sulfate, filtered and concentrated to dry by reducing pressure, obtaining the target compound B-2-5.

Step 5: Synthesis of Compound B-2-6

Compound B-2-5 (10.22 g, 29.17 mmol, 1 eq) was dissolved in water (100 mL) and glacial acetic acid (100 mL) to perform reaction at 100° C. for 16 hours. After the reaction was completed, the solvent was vacuum dried by rotation at 60° C., and then dried with toluene three times to obtain compound B-2-6.

Step 6: Synthesis of Compound B-2-7

Compound B-2-6 (9.52 g, 30.68 mmol, 1 eq) and acetic anhydride (25.05 g, 245.41 mmol, 22.98 mL, 8 eq) were dissolved in pyridine (40 mL), and stirred at 25° C. for 16 hours. After the reaction was completed, the reaction solution was diluted with ethyl acetate (200 mL), washed with 1M dilute hydrochloric acid (100 mL×4). The organic phase was collected and washed with water (50 mL×2), and then washed with a saturated saline solution (50 mL×2), and finally was dried with anhydrous sodium sulfate, and filtered and concentrated to dry by reducing pressure, obtaining a crude product. The crude product was purified by column chromatography (petroleum ether/ethyl acetate system) to obtain the target compound B-2-7.

Step 7: Synthesis of Compound B-2-8

Compound B-2-7 (7 g, 14.63 mmol, 1 eq) and potassium acetate (5.74 g, 58.52 mmol, 4 eq) were dissolved in acetic acid (135 mL) and water (15 mL). Palladium dichloride (5.71 g, 32.18 mmol, 2.2 eq) was added in an ice bath under nitrogen protection to perform reaction at 25° C. for 16 hours. After the reaction was completed, the reaction solution was vacuum dried by rotation at 45° C. to obtain a crude product. The crude product was purified by column chromatography (petroleum ether/ethyl acetate system) to obtain the target compound B-2-8.

Step 8: Synthesis of Compound B-2

Compound B-2-8 (2.5 g, 5.70 mmol, 1 eq) was dissolved in dichloromethane (40 mL), then triphenylphosphine (2.24 g, 8.55 mmol, 1.5 eq) was added thereto, and stirring was performed under nitrogen protection for 30 minute. The mixture was cooled to 0° C., then N-bromosuccinimide (1.52 g, 8.55 mmol, 1.5 eq) was added thereto, and stirring was performed at 25° C. for 2.5 hours. After the reaction was completed, the reaction solution was concentrated to dry at 25° C. to obtain a crude product. The crude product was purified by column chromatography (petroleum ether/ethyl acetate system) to obtain the target compound B-2. $^1$H NMR (400 MHz, CHLOROFORM-d) δ ppm 1.85 (s, 3H), 2.01 (s, 3H), 2.1 (s, 3H), 2.19 (s, 3H), 2.37 (s, 3H) 4.43-4.50 (m, 2H), 4.80-4.83 (d, J=10.4 Hz, 1H), 5.055-5.104 (m, 1H), 5.214-5.249 (m, 1H), 5.553-5.602 (m, 1H), 6.444-6.453 (m, 1H), 7.145-7.165 (m, 1H), 7.209-7.224 (m, 1H), 7.251-7.270 (m, 1H).

Reference Example 11: Fragment B-3

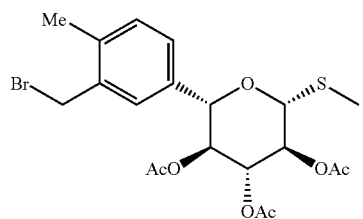 [SMILES: CS[C@H]1O[C@@H](c2ccc(C)c(CBr)c2)[C@H](OC(C)=O)[C@@H](OC(C)=O)[C@@H]1OC(C)=O]

Synthesis Route:

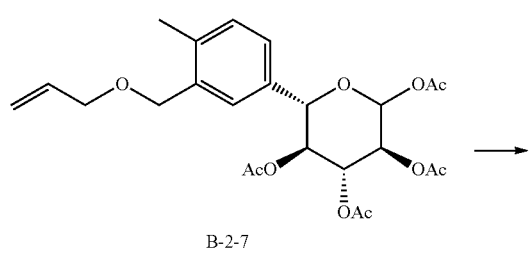

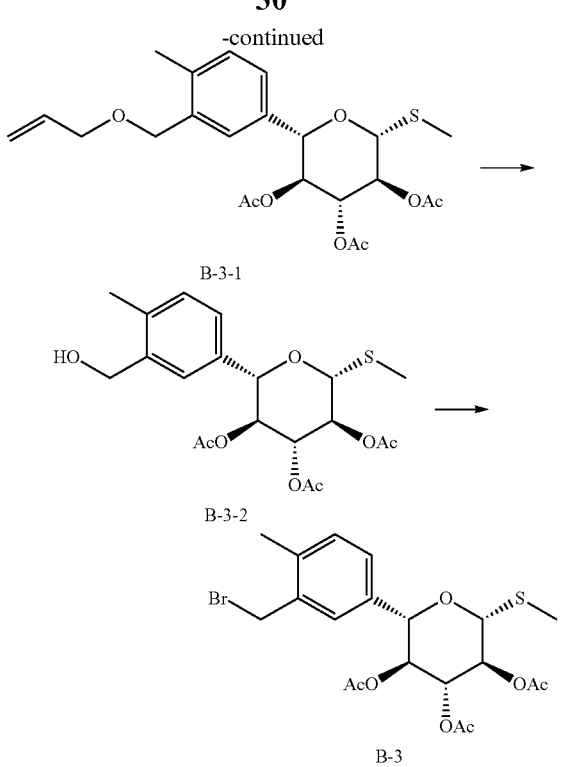

Step 1: Synthesis of Compound B-3-1

Compound B-2-7 (8.8 g, 18.39 mmol, 1 eq) was dissolved in 1,4-dioxane (100 mL), and thiourea (4.20 g, 55.17 mmol, 3 eq) was added thereto. After replaced with nitrogen three times, trimethylsilyl trifluoromethanesulfonate (14.31 g, 64.37 mmol, 3.5 eq) was added thereto at 25° C., and the resulted was heated to 60° C. to perform reaction for 2 hours, and then cooled to 25° C. Methyl iodide (13.30 g, 93.70 g mmol, 5.09 eq) and diisopropylethylamine (19.02 g, 147.13 mmol, 8 eq) were added successively thereto to perform reaction at 25° C. for 14 hours. After the reaction was completed, the reaction solution was diluted with water (80M1), extracted with ethyl acetate (80 mL×3) to collect organic phases. The combined organic phases were with a saturated saline solution (50 mL), dried with anhydrous sodium sulfate, and filtered to obtain a filtrate. The filtrate was dried by rotation under reduced pressure to obtain a crude product. The crude product was purified by column chromatography (petroleum ether/ethyl acetate system) to obtain the target compound B-3-1, which was confirmed by LCMS.

Step 2: Synthesis of Compound B-3-2

Compound B-3-1 (2 g, 4.29 mmol, 1 eq), barbituric acid (1.10 g, 8.57 mmol, 2 eq) and ethanol (20 mL) were added to a reaction flask. After replaced with nitrogen three times, tetra-triphenylphosphine palladium (495.37 mg, 428.68 µmol, 0.1 eq) was added thereto to perform reaction at 70° C. under nitrogen atmosphere for 16 hours. After the reaction was completed, the reaction solution was diluted with water (20 mL) and extracted with ethyl acetate (20 mL×3). The combined organic phases were washed with a saturated saline solution (20 mL), dried with anhydrous sodium sulfate, and filtered to obtain a filtrate. The filtrate was dried by rotation under reduced pressure to obtain a crude product. The crude product was purified by column chromatography (petroleum ether/ethyl acetate system) to obtain the target compound B-3-2, which was confirmed by LCMS.

Step 3: Synthesis of Compound B-3

Compound B-3-2 (1.5 g, 3.52 mmol, 1 eq), triphenylphosphine (1.38 g, 5.28 mmol, 1.5 eq) and dichloromethane (20 mL) were added to a reaction flask. After replacing nitrogen three times, stirring was performed at 25° C. for 0.5 hours, then N-bromosuccinimide (938.98 mg, 5.28 mmol, 1.5 eq) was added thereto at 0° C. to perform reaction at 25° C. for 1.5 hours. After the reaction was completed, the reaction solution was diluted with water (20 mL) and extracted with ethyl acetate (20 mL×3). The combined organic phases were dried with anhydrous sodium sulfate, filtered to obtain a filtrate. The filtrate was dried by rotation under reduced pressure to obtain a crude product. The crude product was purified by column chromatography (petroleum ether/ethyl acetate system) to obtain the target compound B-3. $^1$H NMR (400 MHz, CHLOROFORM-d) δ=7.25 (d, J=6.4 Hz, 2H), 7.18 (d, J=8.4 Hz, 1H), 5.38 (t, J=9.6 Hz, 1H), 5.25 (t, J=9.6 Hz, 1H), 5.13 (t, J=9.6 Hz, 1H), 4.56 (d, J=9.6 Hz, 1H), 4.53 (q, J=10.4 Hz, 2H), 4.43 (d, J=9.6 Hz, 1H), 2.40 (s, 3H), 2.21 (s, 3H), 2.11 (s, 3H), 2.02 (s, 3H), 1.84 (s, 3H).

The fragment B-4 in the following table is synthesized with reference to the steps 1-8 in Reference Example 9. The fragment B-5 in the following table is synthesized with reference to the steps 1-8 in Reference Example 10. The structures in the table also include their possible isomers.

| Reference Example | Fragment B | Structure | $^1$H NMR |
|---|---|---|---|
| 12 | B-4 | 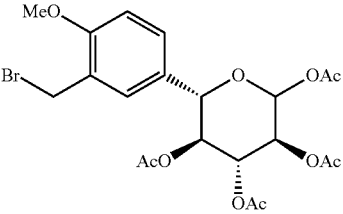 | $^1$H NMR (400MHz, CHLOROFORM-d) δ = 7.33-7.27 (m, 2H), 6.85 (m, J = 8.4 Hz, 1H), 5.87 (d, J = 8.2 Hz, 1H), 5.40-5.32 (t, 1H), 5.31-5.22 (m, 1H), 5.15 (m, J = 9.7 Hz, 1H), 4.64-4.54 (m, 1H), 4.48 (dd, J = 9.8, 13.6 Hz, 2H), 3.92-3.85 (d, 3H), 2.21 (s, 1H), 2.11 (s, 2H), 2.08-2.04 (d, 3H), 2.04-1.99 (d, 3H), 1.89-1.83 (d, 3H) |
| 13 | B-5 | 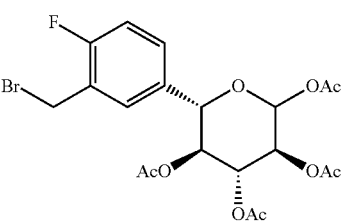 | $^1$H NMR(400 MHz, CHLOROFORM-d) δ ppm 1.85 (s, 1.5H) 1.87 (s, 1.5H) 2.00 (s, 1.5H) 2.02 (s, 1.5H) 2.04 (s, 1.5H) 2.06 (s, 1.5H) 2.09-2.13 (m, 1.5H) 2.20 (s, 1.5H) 4.39-4.46 (m, 1H) 4.49 (br s, 0.5H) 4.53 (d, J = 10.29 Hz, 1H) 4.84 (d, J = 10.04 Hz, 0.5H) 5.01-5.14 (m, 1H) 5.20-5.29 (m, 1H) 5.33-5.39 (m, 0.5H) 5.58 (t, J = 9.91 Hz, 0.5H) 5.86 (d, J = 8.28 Hz, 0.5H) 6.45 (d, J = 3.76 Hz, 0.5H) 7.04 (td, J = 9 03, 2.26 Hz, 1H) 7.29-7.32 (m, 1H) 7.34-7.37 (m, 1H) |

The fragment B-6 in the following table is synthesized with reference to the steps 1-3 in Reference Example 11. The structures in the table also include their possible isomers.

| Reference Example | Fragment | Structure | NMR |
|---|---|---|---|
| 14 | B-6 | 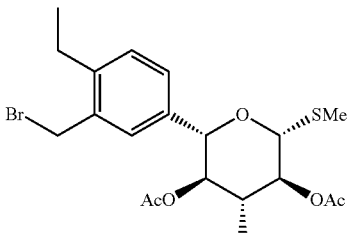 | $^1$H NMR(400 MHz, CHLOROFORM-d) δ ppm 7.28-7.32 (m, 1H) 7.26 (s, 1H) 7.18-7.25 (m, 1H) 5.31-5.41 (m, 1H) 5.19-5.26 (m, 1H) 5.12 (t, J = 9.69 Hz, 1H) 4.47-4.60 (m, 3H) 4.43 (d, J = 9.88 Hz, 1H) 2.76 (q, J = 7.63 Hz, 2H) 2.17-2.25 (m, 3H) 2.07-2.14 (m, 3H) 1.98-2.06 (m, 3H) 1.80-1.90 (m, 3H) 1.28 (t, J = 7.57 Hz, 3H) |

Example 1: WXD001
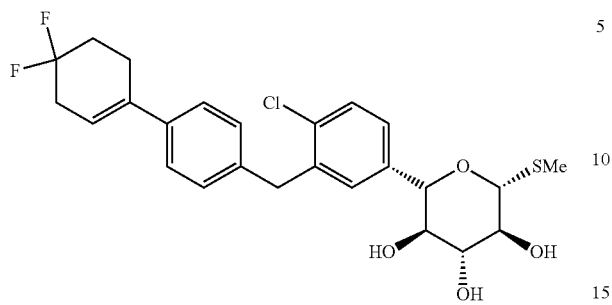
Synthesis Route:
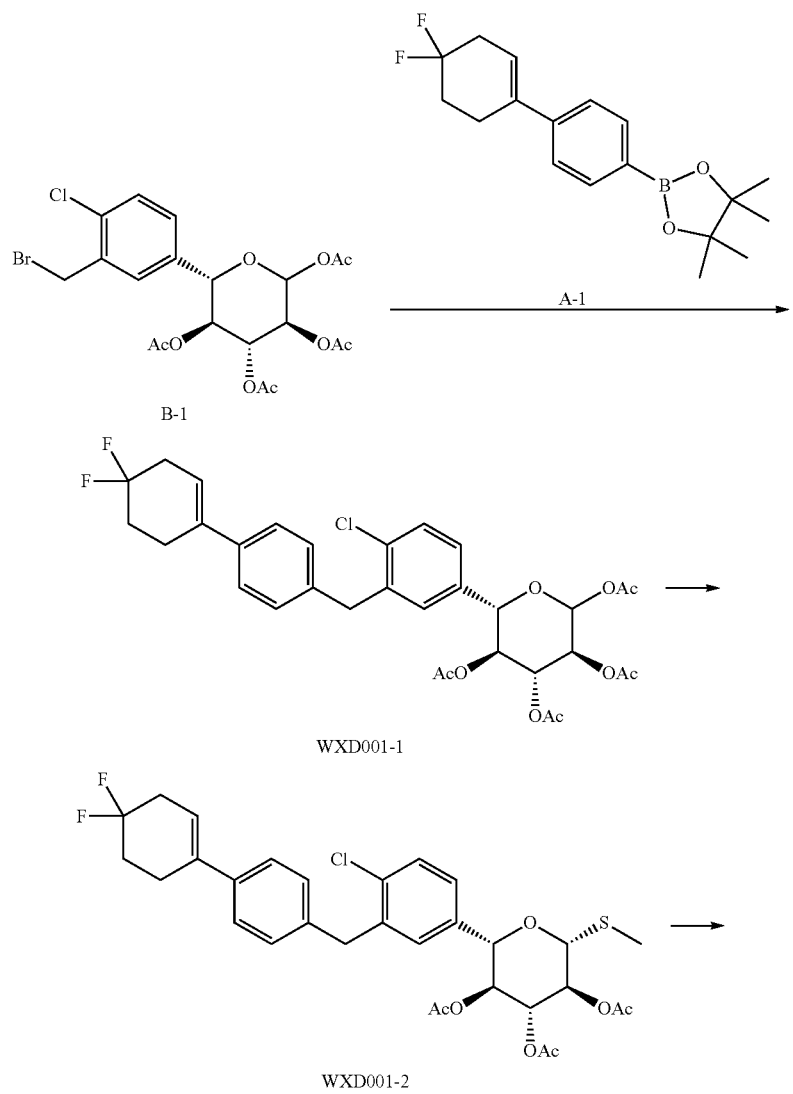

-continued

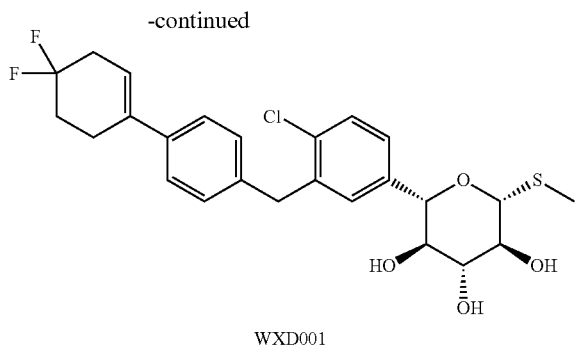

WXD001

Step 1: Synthesis of Compound WXD001-1.

Compound B-1 (1 g, 1.92 mmol, 1 eq) was mixed with compound A-1 (797.78 mg, 2.49 mmol, 1 mL, 1.3 eq), sodium carbonate (2 M, 1.92 mL, 2 eq), toluene (20 mL), ethanol (5 mL) and water (5 mL). After purging nitrogen, tetra-triphenylphosphine palladium (221.48 mg, 191.67 µmol, 0.1 eq) was added thereto to perform reaction at 50° C. for 16 hours, and the reaction solution turned black. After the reaction was completed, the reaction solution was concentrated with a water pump under reduced pressure at 45° C. to remove ethanol, and then concentrated with an oil pump to remove toluene and water, obtaining a crude product. The crude product was purified by column chromatography (petroleum ether/ethyl acetate system) to obtain the target compound WXD001-1. $^1$H NMR (400 MHz, CHLOROFORM-d) δ=7.37 (d, J=8.2 Hz, 1H), 7.30 (d, J=8.2 Hz, 2H), 7.20 (dd, J=2.1, 8.3 Hz, 1H), 7.16-7.07 (m, 3H), 5.89 (dd, J=2.1, 3.4 Hz, 1H), 5.84 (d, J=8.2 Hz, 1H), 5.38-5.29 (m, 1H), 5.25 (dd, J=8.3, 9.6 Hz, 1H), 5.09 (t, J=9.6 Hz, 1H), 4.47 (d, J=9.7 Hz, 1H), 4.12-4.00 (m, 2H), 2.76-2.65 (m, 4H), 2.21-2.14 (m, 2H), 2.13-2.08 (m, 3H), 2.07-2.05 (m, 3H), 2.03-2.00 (m, 3H), 1.74-1.69 (m, 3H).

Step 2: Synthesis of Compound WXD001-2.

Compound WXD001-1 (1 g, 1.57 mmol, 1 eq), thiourea (239.73 mg, 3.15 mmol, 2 eq) and dioxane (12 mL) were added to a reaction flask. After purging nitrogen, trimethylsilyl trifluoromethanesulfonate (874.97 mg, 3.94 mmol, 711.35 uL, 2.5 eq) was added thereto, and slowly heated to 80° C. to perform reaction for 2 hours. After cooling to 25° C., diisopropylethylamine (1.02 g, 7.87 mmol, 1.37 mL, 5 eq) and methyl iodide (670.52 mg, 4.72 mmol, 294.09 uL, 3 eq) were added successively thereto to perform reaction 25° C. for 14 hours. After the reaction was completed, the reaction solution was diluted with water (5 mL), extracted with dichloromethane (2 mL×3) to obtain organic phases. The organic phases were washed with a saturated saline solution (10 mL), dried with anhydrous sodium sulfate, and filtered to obtain a filtrate. The filtrate was concentrated to dry at 45° C. with a water pump to obtain a crude product. The crude product was purified by column chromatography (petroleum ether/ethyl acetate system) to obtain the target compound WXD001-2. $^1$H NMR (400 MHz, CHLOROFORM-d) δ=7.37 (d, J=8.2 Hz, 1H), 7.30 (d, J=8.2 Hz, 2H), 7.19 (dd, J=2.0, 8.3 Hz, 1H), 7.14-7.08 (m, 3H), 5.89 (br s, 1H), 5.31 (s, 1H), 5.19 (s, 1H), 5.04 (s, 1H), 4.50 (d, J=9.9 Hz, 1H), 4.38 (d, J=9.9 Hz, 1H), 4.08 (d, J=17.0 Hz, 2H), 2.69 (m, J=6.0, 8.1 Hz, 4H), 2.24-2.16 (m, 2H), 2.15 (s, 3H), 2.09 (s, 3H), 2.00 (s, 3H), 1.71 (s, 3H).

Step 3: Synthesis of Compound WXD001.

Compound WXD001-2 (760 mg, 1.22 mmol, 1 eq), methanol (6 mL) and tetrahydrofuran (3 mL) were added to a reaction flask, and then lithium hydroxide monohydrate (1.02 g, 24.39 mmol, 20 eq) and water (6 mL) were added thereto to perform reaction at 25° C. for 16 hours. After the reaction was completed, the reaction solution was diluted with water (10 mL), extracted with ethyl acetate (10 mL×3) to obtain organic phases. The organic phases were washed with a saturated saline solution (30 mL), dried with anhydrous sodium sulfate, and filtered to obtain a filtrate. The filtrate was concentrated to dry at 45° C. with a water pump to obtain a crude product. The crude product, was purified by preparative high performance liquid chromatography (acetonitrile/water-aqua ammonia system) to obtain the target compound WXD001. SFC showed that the enantiomeric excess ratio was 100%. $^1$H NMR (400 MHz, METHANOL-$d_4$) δ=7.37 (d, J=8.2 Hz, 1H), 7.34-7.30 (m, 2H), 7.28-7.23 (m, 2H), 7.16 (d, J=8.4 Hz, 2H), 6.00-5.84 (m, 1H), 4.38 (d, J=9.5 Hz, 1H), 4.14 (d, J=9.5 Hz, 1H), 4.11-4.04 (m, 2H), 3.48-3.42 (t, 1H), 3.39-3.32 (m, 2H), 2.72-2.63 (m, 4H), 2.23-2.12 (m, 2H), 2.12 (s, 3H).

Example 2: WXD002

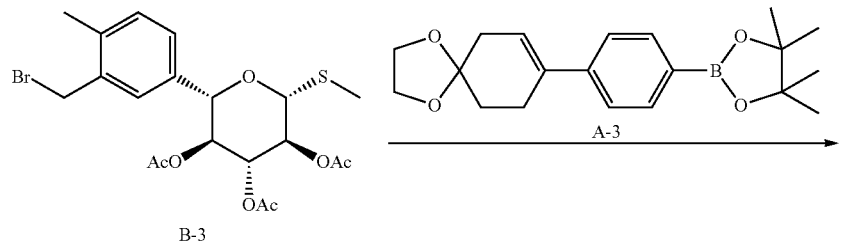

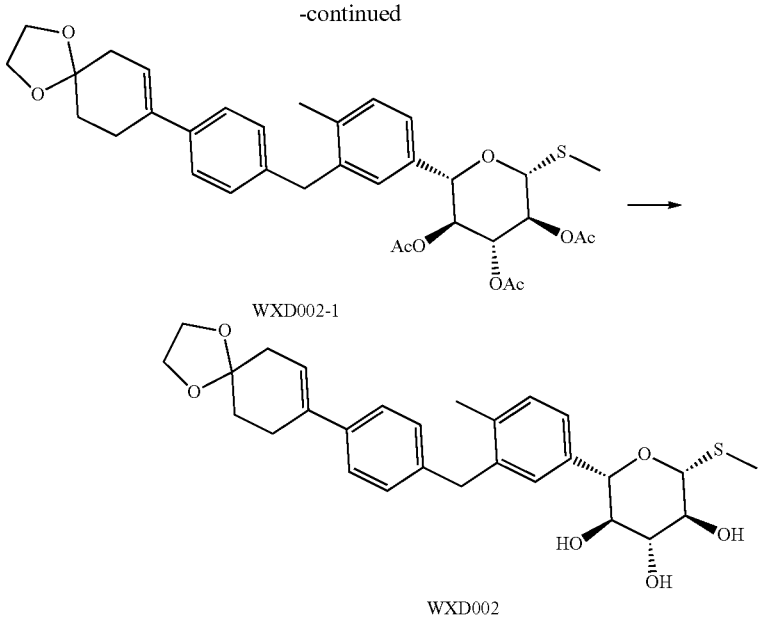

WXD002-1

WXD002

Synthesis Route:

Step 1: Synthesis of Compound WXD002-1.

Compound B-3 (40 mg, 81.74 μmol, 1 eq), compound A-3 (41.96 mg, 122.61 μmol, 1.5 eq), sodium carbonate (17.33 mg, 163.47 μmol, 2 eq), toluene (3 mL), ethanol (0.3 mL) and water (0.3 mL) were added to a reaction flask. After purging nitrogen three times, tetra-triphenylphosphine palladium (9.45 mg, 8.17 μmol, 0.1 eq) was added thereto to perform reaction at 50° C. for 5 hours under a nitrogen atmosphere. After the reaction was completed, the reaction solution was diluted with water (5 mL), extracted with ethyl acetate (5 mL×3) to obtain organic phases. The combined organic phases were dried with anhydrous sodium sulfate, filtered to obtain a filtrate. The filtrate was dried by rotation under reduced pressure to obtain a crude product. The crude product was purified by preparative TLC (petroleum ether/ethyl acetate system) to obtain the target compound WXD002-1. $^1$H NMR (400 MHz, CHLOROFORM-d)=7.30 (d, J=8.0 Hz, 2H), 7.17-7.12 (m, 2H), 7.03-6.99 (m, 3H), 5.96 (t, J=3.6 Hz, 1H), 5.35 (t, J=9.2 Hz, 1H), 5.23 (t, J=9.6 Hz, 1H), 5.14 (t, J=9.6 Hz, 1H), 4.53 (d, J=10.0 Hz, 1H), 4.39 (d, J=10.0 Hz, 1H), 4.02 (s, 4H), 3.94 (d, J=6.8 Hz, 2H), 2.66-2.62 (m, 2H), 2.46-2.45 (m, 2H), 2.02 (s, 3H), 2.17 (s, 3H), 2.10 (s, 3H), 2.01 (s, 3H), 1.93 (t, J=6.4 Hz, 2H), 1.74 (s, 3H).

Step 2: Synthesis of WXD002

Compound WXD2-1 (42 mg, 67.23 μmol, 1 eq), methanol (1 mL), tetrahydrofuran (0.5 mL), water (1 mL), and lithium hydroxide monohydrate (56.42 mg, 1.34 mmol, 20 eq) were added to a reaction flask to perform reaction at 25° C. for 1 hour. After the reaction was completed, the reaction solution was diluted with water (5 mL) and extracted with ethyl acetate (5 mL×4) to obtain organic phases. The combined organic phases were dried over anhydrous sodium sulfate, and filtered to obtain a filtrate. The filtrate was dried by rotation under reduced pressure to obtain a crude product. The crude product was purified by preparative high performance liquid chromatography mechanical separation (acetonitrile/water-aqua ammonia system) to obtain the target compound WXD02. $^1$H NMR (400 MHz, CHLOROFORM-d) δ=7.30 (d, J=8.4, 2H), 7.18-7.13 (m, 3H), 7.09 (d, J=8.0 Hz, 2H), 5.95 (t, J=3.6 Hz, 1H), 4.40 (d, J=9.6 Hz, 1H), 4.14 (d, J=9.2 Hz, 1H), 3.99-3.97 (m, 6H), 3.48-3.35 (m, 3H), 2.62-2.58 (m, 2H), 2.41 (s, 2H), 2.21 (s, 3H), 2.13 (s, 3H), 1.89 (t, J=6.4 Hz, 2H).

Each fragment of the Examples 3-9 in the following table 1 was synthesized with reference to the steps 1-3 in Example 1. The structures in table 1 also include their possible isomers.

TABLE 1

| Reference Example | Fragment A | Fragment B | Compound | Structure |
|---|---|---|---|---|
| 3 | A-1 | B-2 | WXD003 | 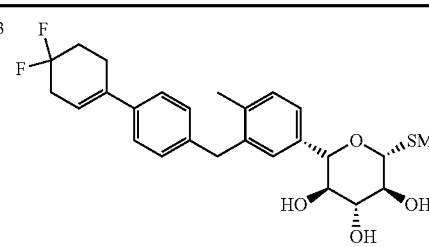 |

TABLE 1-continued
| Reference Example | Fragment A | Fragment B | Compound | Structure |
|---|---|---|---|---|
| 4 | 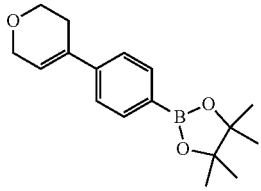 A-2 | 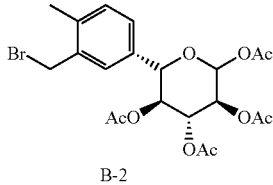 B-2 | WXD004 | 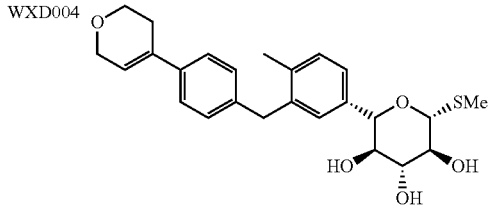 |
| 5 | 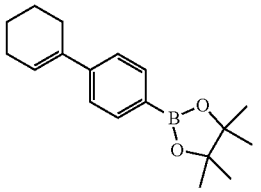 A-4 | 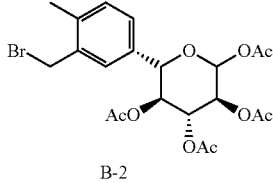 B-2 | WXD005 | 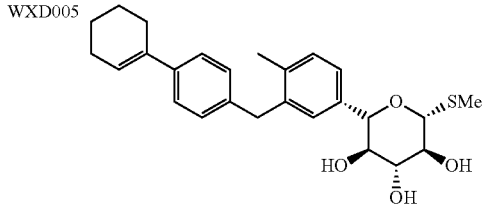 |
| 6 | 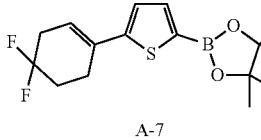 A-7 | 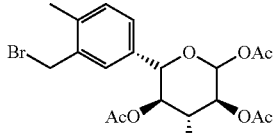 B-2 | WXD006 | 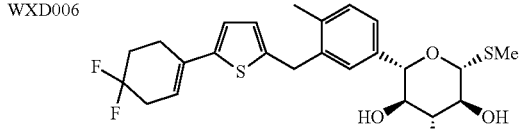 |
| 7 | 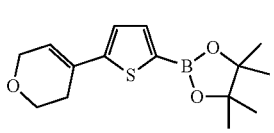 A-8 | 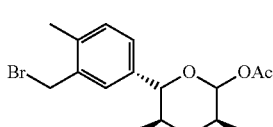 B-2 | WXD007 | 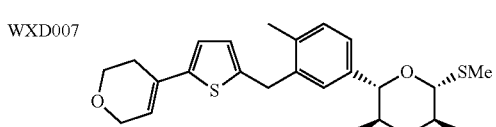 |
| 8 | 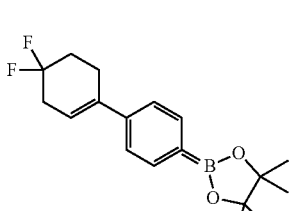 A-1 | 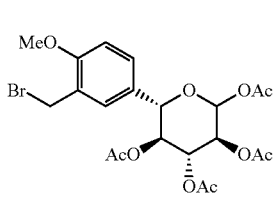 B-4 | WXD008 | 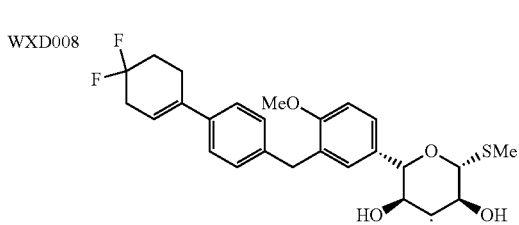 |
| 9 | 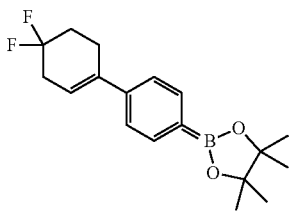 A-1 | 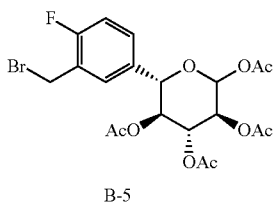 B-5 | WXD009 | 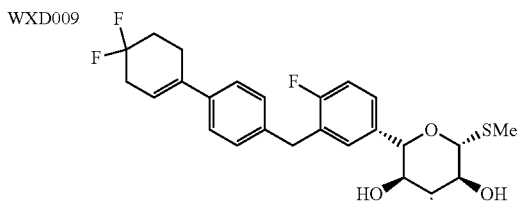 |

Each fragment in Example 10 in the following table 2 was synthesized with reference to the steps 1-2 in Example 2. The structures in table also include their possible isomers.

TABLE 2

| Reference Example | Fragment A | Fragment B | Compound | Structure |
|---|---|---|---|---|
| 10 | 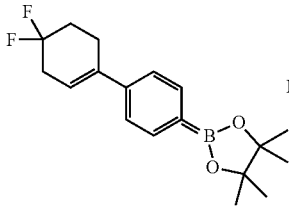<br>A-1 | 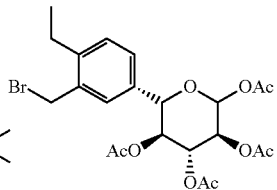<br>B-6 | WX010 | 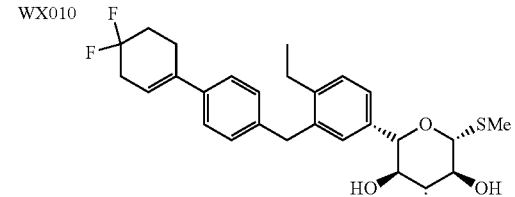 |

The hydrogen spectrum and mass spectrum data of each example are shown in Table 3.

TABLE 3

| Reference Example | Compound | NMR | MS m/z |
|---|---|---|---|
| 1 | WXD001 | $^1$H NMR (400 MHz, METHANOL-$d_4$) δ = 7.37 (d, J = 8.2 Hz, 1 H), 7.34-7.30 (m, 2 H), 7.28-7.23 (m, 2 H), 7.16 (d, J = 8.4 Hz, 2 H), 6.00-5.84 (m, 1 H), 4.38 (d, J = 9.5 Hz, 1 H), 4.14 (d, J = 9.5 Hz, 1 H), 4.11-4.04 (d, 2 H), 3.48-3.42 (t, 1 H), 3.39-3.32 (m, 2 H), 2.72-2.63 (m, 4 H), 2.23-2.12 (m, 2 H), 2.12 (s, 3 H). | 519 (M + Na) |
| 2 | WXD002 | $^1$H NMR (400 MHz, CHLOROFORM-d) δ = 7.30 (d, J = 8.4 Hz, 2 H), 7.18-7.13 (m, 3 H), 7.09 (d, J = 8.0 Hz, 2 H), 5.95 (t, J = 3.6 Hz, 1 H), 4.40 (d, J = 9.6 Hz, 1 H), 4.14 (d, J = 9.2 Hz, 1 H), 3.99-3.97 (m, 6H), 3.48-3.35 (m, 3 H), 2.62-2.58 (m, 2 H), 2.41 (s, 2 H), 2.21 (s, 3 H), 2.13 (s, 3 H), 1.89 (t, J = 6.4 Hz, 2 H). | 521 (M + Na) |
| 3 | WXD003 | $^1$H NMR (400 MHz, METHANOL-$d_4$) δ ppm 2.07-2.18 (m, 5 H), 2.20 (s, 3 H), 2.61-2.74 (m, 4 H), 3.33-3.49 (m, 3 H), 3.98 (s, 2 H), 4.12 (d, J = 9.03 Hz, 1 H), 4.38 (d, J = 9.54 Hz, 1 H), 5.90 (br s, 1 H), 7.06-7.20 (m, 5 H), 7.30 (d, J = 8.28 Hz, 2 H). | 499 (M + Na) |
| 4 | WXD004 | $^1$H NMR (400 MHz, METHANOL-$d_4$) δ ppm 2.14 (s, 3 H), 2.21 (s, 3 H), 2.49 (br dd, J = 4.44, 2.69 Hz, 2 H), 3.35-3.49 (m, 3 H), 3.91 (t, J = 5.50 Hz, 2 H), 3.99 (s, 2 H), 4.13 (d, J = 9.01 Hz, 1 H), 4.28 (q, J = 2.79 Hz, 2 H), 4.39 (d, J = 9.38 Hz, 1 H), 6.13 (br s, 1 H), 7.11 (d, J = 8.13 Hz, 2 H), 7.14-7.20 (m, 3 H), 7.33 (d, J = 8.25 Hz, 2 H). | 465 (M + Na) |
| 5 | WXD005 | $^1$H NMR (400 MHz, METHANOL-$d_4$) δ ppm 1.60-1.70 (m, 2 H), 1.74-1.82 (m, 2 H), 2.13 (s, 3 H), 2.15-2.20 (m, 2 H), 2.21 (s, 3 H), 2.32-2.42 (m, 2 H), 3.33-3.51 (m, 3 H), 3.96 (s, 2 H), 4.13 (d, J = 9.03 Hz, 1 H), 4.39 (d, J = 9.54 Hz, 1 H), 6.06 (dt, J = 3.58, 2.10 Hz, 1 H), 7.06 (d, J = 8.28 Hz, 2 H), 7.11-7.20 (m, 3 H), 7.26 (d, J = 8.28 Hz, 2 H). | 463 (M + Na) |
| 6 | WXD006 | $^1$H NMR (400 MHz, CHLOROFORM-d) δ ppm 7.09-7.17 (m, 3 H), 6.68 (d, J = 3.5 Hz, 1 H), 6.50 (d, J = 3.5 Hz, 1 H), 5.77 (br s, 1 H), 4.33 (br d, J = 9.5 Hz, 1 H) 4.13 (br d, J = 9.0 Hz, 1 H) 4.01 (s, 2 H), 3.61-3.70 (m, 1 H), 3.45-3.56 (m, 2 H), 2.78 (br s, 1 H), 2.41-2.66 (m, 5 H), 2.22 (s, 3 H), 2.13 (s, 3 H), 1.99-2.11 (m, 2 H), 1.95 (br s, 1 H) | 505 (M + Na) |
| 7 | WXD007 | $^1$H NMR (400 MHz, METHANOL-$d_4$) δ ppm 2.15 (s, 3 H), 2.28 (s, 3 H), 2.45 (br d, J = 1.51 Hz, 2 H), 3.35-3.50 (m, 3 H), 3.86 (t, J = 5.52 Hz, 2 H), 4.10 (s, 2 H), 4.14 (d, J = 9.29 Hz, 1 H), 4.21 (br d, J = 2.51 Hz, 2 H), 4.39 (d, J = 9.54 Hz, 1 H), 5.97 (br s, 1 H), 6.61 (d, J = 3.51 Hz, 1 H), 6.81 (d, J = 3.76 Hz, 1 H), 7.13-7.17 (m, 1 H), 7.18-7.21 (m, 1 H), 7.23 (s, 1 H). | 471 (M + Na) |
| 8 | WXD008 | $^1$H NMR (400MHz, METHANOL-$d_4$) δ = 7.28 (d, J = 8.2 Hz, 2 H), 7.23 (dd, J = 2.1, 8.4 Hz, 1 H), 7.19-7.12 (m, 3 H), 6.93 (d, J = 8.4 Hz, 1 H), 5.90 (br s, 1 H), 4.37(d J = 9.4 Hz, 1 H), 4.08 (d J = 9.0 Hz, 1 H), 3.97-3.89 (m, 2 H), 3.81 (s, 3 H), 3.50-3.36 (m, 3 H), 2.71-2.62 (m, 4 H), 2.20-2.13 (m, 2 H), 2.12 (s, 3 H) | 515 (M + Na) |
| 9 | WXD009 | $^1$H NMR (400 MHz, METHANOL-$d_4$) δ ppm 2.06 (s, 3 H), 2.07-2.09 (m, 2 H), 2.54-2.69 (m, 4 H), 3.29-3.45 (m, 3 H), 3.94 (d, J = 2.76 Hz, 2 H), 4.09 (d, J = 9.54 Hz, 1 H), 4.34 (d, J = 9.54 Hz, 1 H), 5.87 (br s, 1 H), 6.96-7.04 (m, 1 H), 7.14 (d, J = 8.28 Hz, 2 H), 7.18-7.25 (m, 2 H), 7.28 (d, J = 8.28 Hz, 2 H). | 503 (M + Na) |

TABLE 3-continued

| Reference Example | Compound | NMR | MS m/z |
|---|---|---|---|
| 10 | WXD010 | $^1$H NMR (400 MHz, METHANOL-$d_4$) δ ppm 1.09 (t, J = 7.53 Hz, 3 H), 2.10 (m, 1 H), 2.13 (s, 3 H), 2.14-2.22 (m, 1 H), 2.56-2.74 (m, 6 H), 3.34-3.48 (m, 3 H), 4.02 (s, 2 H), 4.13 (d, J = 9.03 Hz, 1 H), 4.39 (d, J = 9.29 Hz, 1 H), 5.91 (br s, 1 H), 7.10 (d, J = 8.28 Hz, 2 H), 7.14-7.21 (m, 2 H), 7.21-7.25 (m, 1 H), 7.30 (d, J = 8.28 Hz, 2 H). | 513 (M + Na) |

Experiment Example 1. In Vitro Cell Viability Test

Experimental steps and methods:
Biological activity experiment 1: SGLT1 glucose transport test.
1. Purpose of the Experiment:
The effect of the compound on the glucose transport activity of SGLT1 transporter was detected by measuring the amount of [$^{14}$C]-labeled glucose entering cells with high expression of Human-SGLT1.
2. Experimental Methods.
2.1. Cell Preparation.
The cells stably expressing Human-SGLT1 were constructed by Wuxi AppTec (Shanghai) Co., Ltd. SGLT1 cells were laid in Cytostar-T (PerkinElmer) 96-well cell culture plate and cultured overnight in 5% $CO_2$ environment at 37° C.
2.2. SGLT1 Glucose Transport Test.
1) Experimental buffer, including: 10 mM 4-hydroxyethylpiperazineethanesulfonic acid (HEPES), 1.2 mM magnesium chloride ($MgCl_2$), 4.7 mM potassium chloride (KCl), 2.2 mM calcium chloride ($CaCl_2$) and 120 mM sodium chloride (NaCl).
2) Compounds were serially diluted in 100% dimethyl sulfoxide (DMSO) starting at 1 mM and make a 5-folds, 8 points serials compound dilutions.
3) 3 μM [$^{14}$C]-labeled methyl a-D-glucopyranosid was prepared with the experimental buffer.
4) The cells were treated with 49 uL of the experimental buffer, 1 μL of the gradient diluted compound and 50 μL of the 3 μM [$^{14}$C]-labeled methyl a-D-lucopyranosid solution at 37° C. for 2 hours.
5) The data were read with an isotope detector Micro beta Reader.
6) The $IC_{50}$ value of the tested compound was obtained by the calculation formula: log(inhibitor) vs. response—Variable slope, using GraphPad Prism 5.0 software.

Biological activity experiment 2: SGLT2 glucose transport test.
1. Purpose of the Experiment:
The effect of the compound on the glucose transport activity of SGLT2 transporter was detected by measuring the amount of [$^{14}$C]-labeled glucose entering cells with high expression of Human-SGLT2.
2. Experimental Methods.
2.1. Cell Preparation.
The cells stably expressing Human-SGLT2 were constructed by Wuxi AppTec (Shanghai) Co., Ltd. SGLT2 cells were laid in 96-well cell culture plate (Greiner) and cultured overnight in 5% $CO_2$ environment at 37° C.
2.2. SGLT2 Glucose Transport Test.
1) Experimental buffer, including: 10 mM 4-hydroxyethylpiperazineethanesulfonic acid (HEPES), 1.2 mM magnesium chloride ($MgC_2$), 4.7 mM potassium chloride (KCl), 2.2 mM calcium chloride ($CaCl_2$) and 120 mM sodium chloride (NaCl).
2) Stop buffer, including: 10 mM 4-hydroxyethylpiperazineethanesulfonic acid (HEPES), 1.2 mM magnesium chloride ($MgCl_2$), 4.7 mM potassium chloride (KCl), 2.2 mM calcium chloride ($CaC_2$), 120 mM sodium chloride (NaCl) and 1 μM LX4211.
3) Compounds were serially diluted in 100% dimethyl sulfoxide (DMSO) starting at 10 uM and make a 5-folds, 8 points serials compound dilutions.
4) 6 μM [$^1$C]-labeled methyl a-D-lucopyranosid was prepared with the experimental buffer.
5) The cells were treated with 49 uL of the experimental buffer, 1 μL of the gradient diluted compound and 50 μL of the 6 μM [$^{14}$C]-labeled methyl a-D-lucopyranosid solution at 37° C. for 2 hours.
6) The solution was sucked out from holes, and the cells were rinsed with the stop buffer for 3 times.
7) The cells were lysed with 50 ul of 10% sodium hydroxide solution, the cell lysate was sucked into a scintillation tube, into which 2 mL scintillation solution was then added.
8) The data were read with an isotope detector Tricarb.
9) The $IC_{50}$ value of the tested compound was obtained by the calculation formula: log(inhibitor) vs. response—Variable slope, using GraphPad Prism 5.0 software.
The experimental results are shown in Table 4:

TABLE 4

Results of cell viability test in vitro

| Compound | Human-SGLT1 $IC_{50}$ (nM) | Human-SGLT2 $IC_{50}$ (nM) |
|---|---|---|
| Sotagliflozin | 69.0 | 1.15 |
| WXD001 | 210 | 3.98 |
| WXD002 | 55.6 | 1.01 |
| WXD003 | 49.5 | 2.04 |
| WXD004 | 14.1 | 1.49 |
| WXD005 | 21.9 | 1.78 |
| WXD006 | 39.2 | 1.02 |
| WXD007 | 30.1 | 1.35 |
| WXD008 | 17.2 | 5.40 |
| WXD009 | 233 | 4.68 |
| WXD010 | 14.8 | 2.49 |

Conclusion: The compound of the present disclosure exhibits superior in vitro inhibitory activity against Human-SGLT1 and Human-SGLT2.

Experimental Example 2. Study on the In Vivo Pharmacokinetics in Animals

Study on the In Vivo Pharmacokinetics in Rats
The purpose of the experiment: Male SD rats were used as test animals and were given a single administration to determine the plasma concentration of the compound and evaluate the pharmacokinetic behavior.

Experimental method: Six healthy adult male SD rats were divided into 2 groups, with 3 rats in an intravenous injection group and 3 rats in an oral administration group. In the intravenous injection group, the test compound was mixed with an appropriate amount of vehicle (10% N-methyl pyrrolidone (NMP)/10% polyethylene glycol-15 hydroxystearate (available from solutol)/80% water), then vortexed and sonicated to prepare 0.2 mg/mL clear solution, which was filtered by microporous membrane. In the oral administration group, 10% N-methyl pyrrolidone (NMP)/10% polyethylene glycol-15 hydroxy stearate (available from solutol)/80% water was used as a vehicle and mixed with the test compound, then vortexed and sonicated to prepare 0.40 mg/mL clear solution. The rats were given intravenous administration at a dose of 1 mg/kg or oral administration at a dose of 2 mg/kg. Whole blood was collected at a certain period of time to prepare the plasma. The drug concentration of the plasma was analyzed by LC-MS/MS method, and the pharmacokinetic parameters were calculated using Phoenix WinNonlin software (Pharsight Company, USA).

The experimental results are shown in Table 5:

TABLE 5

Results of pharmacokinetic (PK) test of compounds

| Compound | $C_{max}$ (nM) | F % | Oral DNAUC (nM · h/mpk) | $Vd_{ss}$ (L/kg) | Cl (mL/min/kg) | $T_{1/2}$ (h) |
|---|---|---|---|---|---|---|
| Sotagliflozin | 364 | 54.8 | 969 | 2.01 | 22.6 | 1.27 |
| WXD001 | 410 | 59.0 | 1823 | 3.86 | 10.1 | 4.59 |
| WXD003 | 391 | 47.7 | 1013 | 2.94 | 14.5 | 2.56 |
| WXD010 | 356 | 56.4 | 2320 | 2.48 | 8.06 | 4.50 |

Notes: $C_{max}$ represents the maximum concentration; F % represents oral bioavailability; Oral DNAUC=$AUC_{PO}$/Dose (unit oral exposure), $AUC_{PO}$ represents oral exposure, Dose is drug dose; $Vd_{ss}$ is distribution volume; Cl is clearance rate; and $T_{1/2}$ is half-life.

Study on the In Vivo Pharmacokinetics in Beagle Dogs

The purpose of the experiment: Male beagle (Beagle) dogs were used as test animals and were given a single administration to determine the plasma concentration of the compound and evaluate the pharmacokinetic behavior.

Experimental method: Six male Beagle dogs were divided into 2 groups, with 3 dogs in an intravenous injection group and 3 dogs in an oral administration group. In the intravenous injection group, the test compound was mixed with an appropriate amount of vehicle (20% polyethylene glycol-400 (PEG400)/10% polyethylene glycol-15 hydroxy stearate (available from solutol)/70% water), then vortexed and sonicated to prepare 1 mg/mL clear solution, which was filtered by microporous membrane. In the oral administration group, 20% polyethylene glycol-400 (PEG400)/10% polyethylene glycol-15 hydroxy stearate (available from solutol)/70% water was used as a vehicle and mixed with the test compound, then vortexed and sonicated to prepare 1 mg/mL clear solution. The dogs were given intravenous administration at a dose of 1 mg/kg or oral administration at a dose of 2 mg/kg. Whole blood was collected at a certain period of time to prepare the plasma. The drug concentration of the plasma was analyzed by LC-MS/MS method, and the pharmacokinetic parameters were calculated using Phoenix WinNonlin software (Pharsight Company, USA).

The experimental results are shown in Table 6:

TABLE 6

Results of pharmacokinetic (PK) test of compounds

| Compound | $C_{max}$ (nM) | F % | Oral DNAUC (nM · h/mpk) | $Vd_{ss}$ (L/kg) | Cl (mL/min/kg) | $T_{1/2}$ (h) |
|---|---|---|---|---|---|---|
| WXD010 | 1287 | 82 | 4051 | 1.49 | 6.9 | 2.4 |

Notes: $C_{max}$ represents the maximum concentration; F % represents oral bioavailability; Oral DNAUC=$AUC_{PO}$/Dose (unit oral exposure), $AUC_{PO}$ represents oral exposure, Dose is drug dose; $Vd_{ss}$ is distribution volume; Cl is clearance rate; $T_{1/2}$ is half-life.

Conclusion: The compound of the present disclosure has good oral exposure and bioavailability.

Experimental Example 3. Study on In Vivo Efficacy of Oral Glucose Tolerance Test (OGTT) in Rats Study on the In Vivo Efficacy of Oral Glucose Tolerance Test (OGTT) in Rats for the First Time:

Summary of the Experiment:

1. Animals:

| Animal: | Species | SD rats | Gender: | Male |
|---|---|---|---|---|
| | Age/weight: | About 8 weeks old/250 g | Supplier: | Shanghai SLAC |
| Animal feed | Ordinary feed for rats and mice | | | |

2. Experimental grouping:

| Groups | Compound | Dose | Administration Frequency | Administration method | Number of animals per group |
|---|---|---|---|---|---|
| 1 | Vehicle control group | 0 | Single administration | Intragastric administration | 5 |
| 2 | Positive compound (Sotagliflozin) | 10 mg/kg | Single administration | Intragastric administration | 5 |
| 3 | WXD001 | 10 mg/kg | Single administration | Intragastric administration | 5 |
| 4 | WXD003 | 10 mg/kg | Single administration | Intragastric administration | 5 |

Experiment Procedure:

1. Animal Adaptation and Preparation:

The experimental animals were allowed to adapt to the environment in the animal room for one week after they arrived.

2. Fasting and Drug Administration.

The animals fasted in the metabolic cage for 18 hours, then were given drugs or vehicle (2 ml/kg) according to the above table, and subsequently were immediately given 50% glucose solution (2 g/kg, 4 ml/kg).

3. Urine Glucose and Blood Glucose Test.

2 hours after the administration of glucose solution, feed intake was restored. Blood samples were taken at 0 min, 15 min, 30 min, 45 min, 60 min and 120 min respectively, and urine samples were collected at 0-24 h to test blood glucose, urine glucose (mg/200 g) and urine volume respectively.

4. Data Analysis:

All values are represented as averages. Statistical analysis was performed using Graphpad Prism 6 one-way analysis of variance and Tukey's multiple comparison test. P value of less than 0.05 is considered statistically significant.

The experimental results are shown in Table 7:

TABLE 7

Results of glucose tolerance test in rats.

| Compound | Vehicle control group | Positive compound (Sotagliflozin) | WXD001 | WXD003 |
|---|---|---|---|---|
| OGTT blood glucose level $AUC_{0-2hr}$ (mol/L × min) | 1033 | 823* | 832* | 797** |
| Urine glucose level (mg/200 g, BW) | 1.8 | 2424.0**** | 2181.4**** | 1636.4**** |
| Urine volume (mL/200 gBW) | 21.36 | 39.74**** | 37.58**** | 24.58 |

Notes:
*$p < 0.05$, $p < 0.01$, $p < 0.001$, ****$p < 0.0001$ vs. vehicle control group.

Study on the In Vivo Efficacy of Oral Glucose Tolerance Test (OGTT) in Rats for the Second Time:

Summary of the Experiment:

| 1. Animals: | | | | |
|---|---|---|---|---|
| Animal: | Species | SD rats | Gender: | Male |
| | Age/weight: | About 8 weeks old/250 g | Supplier: | Shanghai SLAC |
| Animal feed | Ordinary feed for rats and mice | | | |

| 2. Experimental grouping: | | | | | |
|---|---|---|---|---|---|
| Groups | Compound | Dose | Administration Frequency | Administration method | Number of animals per group |
| 1 | Vehicle control group | 0 | Single administration | Intragastric administration | 5 |
| 2 | Positive compound (Sotagliflozin) | 10 mg/kg | Single administration | Intragastric administration | 5 |
| 4 | WXD003 | 10 mg/kg | Single administration | Intragastric administration | 5 |

Experiment Procedure:

1. Animal Adaptation and Preparation:

The experimental animals were allowed to adapt to the environment in the animal room for one week after they arrived.

2. Fasting and Drug Administration.

The animals fasted in the metabolic cage for 18 hours, then were given drugs or vehicle (2 ml/kg) according to the above table, and subsequently were immediately given 50% glucose solution (2 g/kg, 4 ml/kg).

3. Urine Glucose and Blood Glucose Test.

2 hours after the administration of glucose solution, feed intake was restored. Blood samples were taken at 0 min, 15 min, 30 min, 45 min, 60 min and 120 min respectively, and urine samples were collected at 0-24 h to test blood glucose, urine glucose (mg/200 g) and urine volume respectively.

4. Data Analysis:

All values are represented as averages. Statistical analysis was performed using Graphpad Prism 6 one-way analysis of variance and Tukey's multiple comparison test. P value of less than 0.05 is considered statistically significant.

The experimental results are shown in Table 8:

TABLE 8

Results of glucose tolerance test in rats.

| Compound | Vehicle control group | Positive compound (Sotagliflozin) | WXD010 |
|---|---|---|---|
| OGTT blood glucose level $AUC_{0-2hr}$ (mol/L × min) | 1134 | 790**** | 720**** |
| Urine glucose level (mg/200 g, BW) | 0.8 | 2843.2**** | 2118.7**** |
| Urine volume (mL/200 g, BW) | 11.5 | 26.4**** | 20.0**** |

Notes: *$p < 0.05$, $p < 0.01$, $p < 0.001$, ****$p < 0.0001$ vs. vehicle control group.

Conclusion: Compared with the vehicle control group, the compound of the present disclosure can significantly reduce the blood glucose AUC level within 2 hours and increase the 24-hour urine glucose excretion level of animals. Compared with the positive compound, the compound of the present disclosure has a lower level of urine glucose under the same hypoglycemic effect, which is helpful to reduce the side effects of urinary tract infection.

Experimental Example 4: Study on the In Vivo Pharmacodynamics in Diabetic dB/dB Mice Summary of the Experiment:

| 1. Animal information: | |
|---|---|
| Species | db/db mice |
| Grade | SPF animal |
| Age | 5 weeks old |
| The age at which the experiment started | 6 weeks old |
| Body weight range | about 25 g |
| Gender | Male |
| Supplier | Model Animal Research Center of Nanjing University |
| Supplier address | Nanjing, Jiangsu, China |

2. Animal Feeding

The animals were kept in an animal breeding room with strictly controlled environmental conditions after they arrived. The animal breeding room was maintained at a temperature of 20-24° C. and a humidity of 40-70%. The temperature and humidity in the feeding room were monitored in real time by a hygrothermograph, and the temperature and humidity were recorded twice daily (one in the morning and the other in the afternoon). The lighting of the animal feeding room was controlled by an on-off electronic timing system, with lights for 12 hours and dark for 12 hours daily (turned on at 7:00 a.m. and turned off at 19:00 p.m). The mice were raised in separate cages and were given free access to feed (reproductive feed 17053113 for rats and mice, available from Beijing Keao Xieli Feed Co., Ltd.) and water during the experiment.

| Group | Treatment | Administration cycle @ dose | Administration method and frequency | Number of animals per group |
|---|---|---|---|---|
| 1 | Vehicle control group | Weeks 1-4 @ 0 mg/kg Weeks 5-8 @ 0 mg/kg | Intragastric administration, once daily | 6 |
| 2 | WXD003 | Weeks 1-4 @ 5 mg/kg Weeks 5-8 @ 10 mg/kg | Intragastric administration, once daily | 6 |
| 3 | WXD010 | Weeks 1-4 @ 5 mg/kg Weeks 5-8 @ 10 mg/kg | Intragastric administration, once daily | 6 |

3. Experiment grouping:

Experiment Procedure:

1. Administration of Drug

During the experiment, the animals were administrated with the corresponding vehicles or drugs according to the group with an administration time of 16:00 and an administration period of 8 weeks.

The dose was 5 mg/kg from week 1 to week 4; and the dose was 10 mg/kg from week 5 to week 8.

2. Blood Glucose Level

Random and fasting blood glucose levels were measured once a week.

The random blood glucose level was measured at 10:00 a.m.

Fasting blood glucose test: The mice fasted from 10:00 a.m., and blood glucose level was firstly measured at 16:00. Then the mice were administered with the drugs, and 2 hours later blood glucose level was measured again, and then feed intake was restored.

3. Oral Glucose Tolerance Test (OGTT).

At the end of the experiment (i.e. the last 3 days of administration), the animals fasted for 6 hours, then were given a single administration of glucose aqueous solution at a dose of 2 g/kg. The time of the glucose administration was recorded as 0 min. Blood glucose levels of the animals were detected at 0 min before the glucose administration, and 15 min, 30 min, 90 min and 120 min after the glucose administration, respectively. The glucose tolerance curve was drawn according to the data of blood glucose levels vs time, and the area under the curve (AUC) was calculated. The administration was given at 16:00.

4. Biochemical Detection

At weeks 4 and 8 of the experiment, the animals fasted for 6 hours, and blood samples were collected to measure glycosylated hemoglobin.

5. Body Weight and Food Consumption

During the experiment, the body weight of the animals was monitored once daily, and food consumption was monitored twice a week.

6. Data Processing and Analysis

All of the data were entered into an Excel document and expressed in the form of mean S.E.M. The differences between groups were compared using graphpad Prism 6 software and one-way analysis of variance (ANOVA). P value of less than 0.05 is considered a significant difference.

The results of random blood glucose experiment from week 1 to week 8 are shown in Table 9:

TABLE 9

Results of random blood glucose experiment

| Group | Vehicle control group | WXD003 | WXD010 |
|---|---|---|---|
| Week 1 | 27.4 ± 2.26 | 14.3 ± 2.28*** | 16.7 ± 1.00** |
| Week 2 | 21.8 ± 2.09 | 15.7 ± 0.88 | 13.5 ± 2.46* |
| Week 3 | 25.6 ± 2.65 | 13.6 ± 1.40*** | 14.1 ± 0.97*** |
| Week 4 | 27.4 ± 3.33 | 13.3 ± 0.81**** | 15.4 ± 1.34*** |
| Week 5 | 26.9 ± 3.67 | 14.1 ± 1.28** | 13.2 ± 1.09** |
| Week 6 | 28.8 ± 1.84 | 10.1 ± 1.26**** | 10.6 ± 1.48**** |
| Week 7 | 27.2 ± 2.63 | 12.5 ± 1.23**** | 9.8 ± 0.82**** |
| Week 8 | 27.6 ± 2.96 | 14.4 ± 1.77*** | 9.2 ± 0.68**** |

Notes: *$p < 0.05$, $p < 0.01$, $p < 0.001$, ****$p < 0.0001$ vs. vehicle control group.

Conclusion: Compared with the vehicle control group, the compound of the present disclosure can reduce the random blood glucose level of animals; the compound of the present disclosure can further reduce the random blood glucose level of animals with the increase of dose.

The results of fasting blood glucose test from week 1 to week 8 are shown in Table 10:

TABLE 10

Results of fasting blood glucose test

| Group | Vehicle control group | WXD003 | WXD010 |
|---|---|---|---|
| Week 1 | 21.8 ± 3.30 | 14.8 ± 2.34 | 14.7 ± 2.50 |
| Week 2 | 26.8 ± 3.26 | 19.9 ± 1.32 | 14.4 ± 1.47*** |
| Week 3 | 28.7 ± 3.00 | 15.8 ± 1.48** | 15.8 ± 1.40** |
| Week 4 | 28.9 ± 3.35 | 14.3 ± 1.29*** | 14.9 ± 1.24*** |
| Week 5 | 25.7 ± 2.82 | 17.4 ± 1.72* | 15.9 ± 0.79* |
| Week 6 | 28.5 ± 3.15 | 10.9 ± 1.42**** | 11.0 ± 1.67**** |
| Week 7 | 30.0 ± 2.58 | 11.7 ± 1.30**** | 9.6 ± 0.91**** |
| Week 8 | 31.4 ± 1.86 | 13.0 ± 1.36**** | 8.1 ± 0.51**** |

Notes:
*$p < 0.05$, $p < 0.01$, $p < 0.001$, ****$p < 0.0001$ vs. vehicle control group.

Conclusion: Compared with the vehicle control group, the compound of the present disclosure can significantly reduce the fasting blood glucose level of animals; by increasing the dose, the compound of the present disclosure can further reduce the fasting blood glucose level of animals.

The results of oral glucose tolerance test (OGTT) at week 8 are shown in Table 11:

TABLE 11

Results of oral glucose tolerance test (OGTT) at week 8

| Compound | Vehicle control group | WXD003 | WXD010 |
|---|---|---|---|
| OGTT blood glucose level $AUC_{0-2hr}$ (mol/L × min) | 4515.5 ± 160.22 | 2806.5 ± 155.12**** | 2118.4 ± 99.17**** |

Notes: *$p < 0.05$, $p < 0.01$, $p < 0.001$, ****$p < 0.0001$ vs. vehicle control group.

Conclusion: Compared with the vehicle control group, the compound of the present disclosure can significantly reduce the blood glucose level AUC within 2 hours ($AUC_{0-2\,hr}$) of animals.

The results of glycosylated hemoglobin (HbAlc) test at weeks 4 and 8 are shown in Table 12:

TABLE 12

Results of glycosylated hemoglobin (HbA1c) at weeks 4 and 8

| Group | Week 4 HbA1c (%) | Week 4 Rate of Decline of HbA1c (%) | Week 8 HbA1c (%) | Week 8 Rate of Decline of HbA1c (%) |
| --- | --- | --- | --- | --- |
| Vehicle control group | 8.4 | 0 | 9.6 | 0 |
| WXD003 | 5.7*** | −32 | 5.9**** | −39 |
| WXD010 | 5.8*** | −31 | 5.1**** | −47 |

Notes: *p < 0.05, p < 0.01, *p < 0.001, ****p < 0.0001 vs. vehicle control group.

Conclusion: Compared with the vehicle control group, the compound of the present disclosure can significantly reduce the level of glycosylated hemoglobin (HbA1c) of animals; the compound of the present disclosure can further reduce the level of glycosylated hemoglobin (HbA1c) of animals with the increase of dose.

Figure 2:
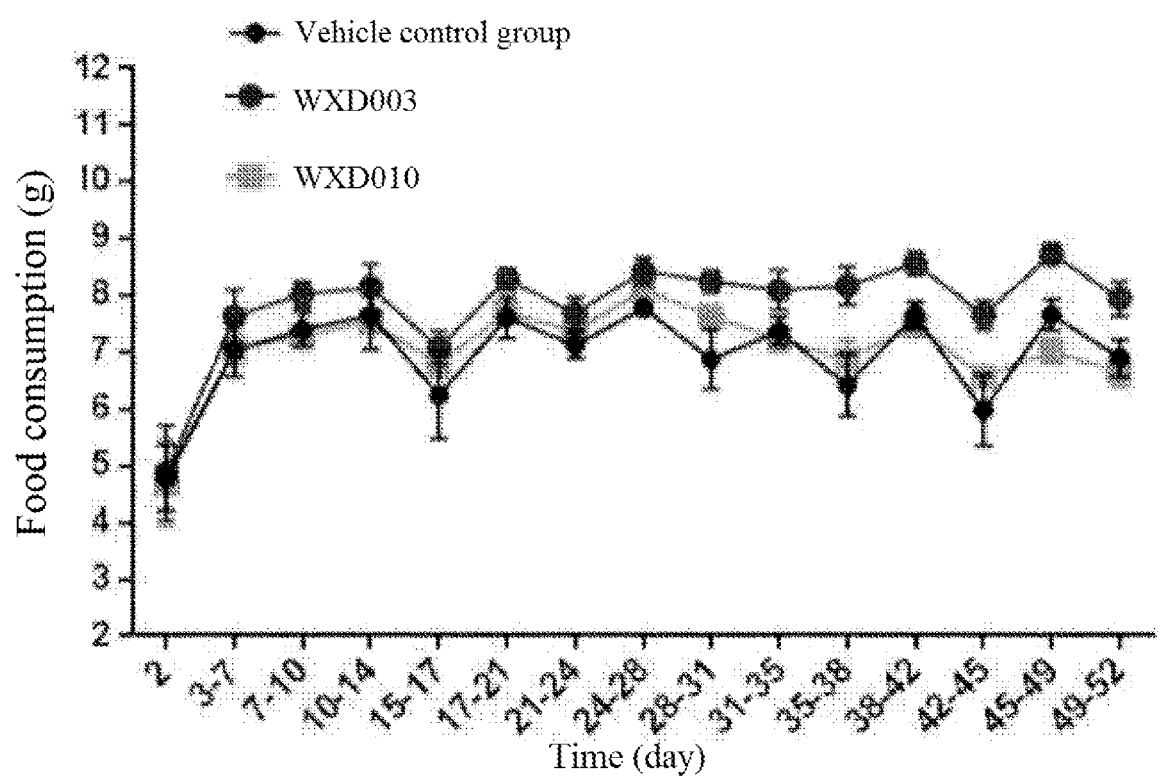
FIG. 2: Results of changes in the food consumption of animal from week 1 to week 8.

The results of body weight and food consumption are shown in FIGS. 1 and 2. It is concluded that after 8 weeks of administration, compared with the vehicle control group, the animals in the administration group did not show significant change in the body weight and food consumption, indicating that the animals have good tolerance to the compound of the present disclosure.

We claim:

1. A compound represented by formula (I), an isomer thereof, or a pharmaceutically acceptable salt thereof,

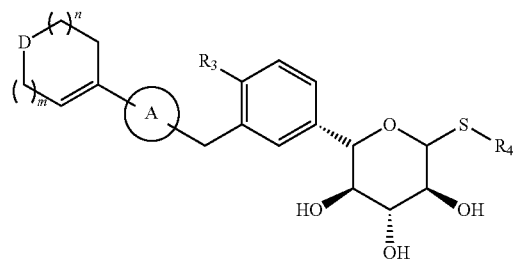

(I)

wherein, m is 1 or 2;
n is 0, 1 or 2;
D is —O— or —C($R_1$)($R_2$)—;
ring A is selected from phenyl and 5-6 membered heteroaryl;
$R_1$ is selected from the group consisting of H, F, Cl, Br, I, OH and $NH_2$;
$R_2$ is selected from the group consisting of H, F, Cl, Br and I;
or $R_1$ and $R_2$ are connected to form a 5-6 membered heterocycloalkyl;
$R_3$ is selected from the group consisting of H, F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by one, two or three R group(s);
$R_4$ is selected from $C_{1-3}$ alkyl, wherein the $C_{1-3}$ alkyl is optionally substituted by one, two or three R group(s);
R is selected from the group consisting of F, Cl, Br, I, OH and $NH_2$; and
the 5-6 membered heteroaryl and 5-6 membered heterocycloalkyl respectively contain one, two, three or four heteroatom(s) or heteroatom group(s) independently selected from the group consisting of —NH—, —O—, —S— and N.

2. The compound, the isomer thereof, or the pharmaceutically acceptable salt thereof according to claim 1, wherein $R_3$ is selected from the group consisting of H, F, Cl, Br, I, OH, $NH_2$, $CH_3$, Et, and —O—$CH_3$.

3. The compound, the isomer thereof, or the pharmaceutically acceptable salt thereof according to claim 1, wherein $R_4$ is selected from $CH_3$ and Et.

4. The compound, the isomer thereof, or the pharmaceutically acceptable salt thereof according to claim 1, wherein the ring A is selected from phenyl and thienyl.

5. The compound, the isomer thereof, or the pharmaceutically acceptable salt thereof according to claim 4, wherein the ring A is selected from

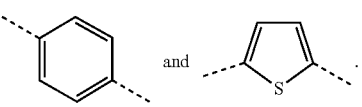

6. The compound, the isomer thereof, or the pharmaceutically acceptable salt thereof according to claim 1, wherein the structural unit

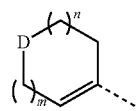

is selected from

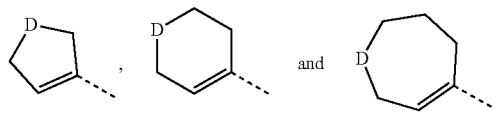

7. The compound, the isomer thereof, or the pharmaceutically acceptable salt thereof according to claim 6, wherein the structural unit

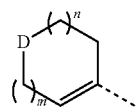

is selected from

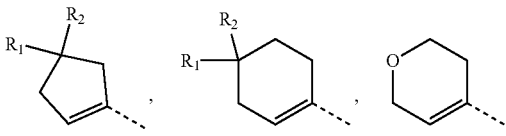

and

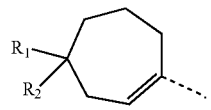

8. The compound, the isomer thereof, or the pharmaceutically acceptable salt thereof according to claim 1, wherein the structural unit

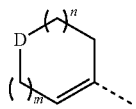

is selected from

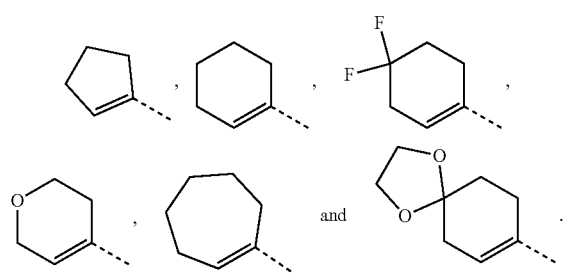

9. The compound, the isomer thereof, or the pharmaceutically acceptable salt thereof according to claim 1, selected from the group consisting of (I-1)

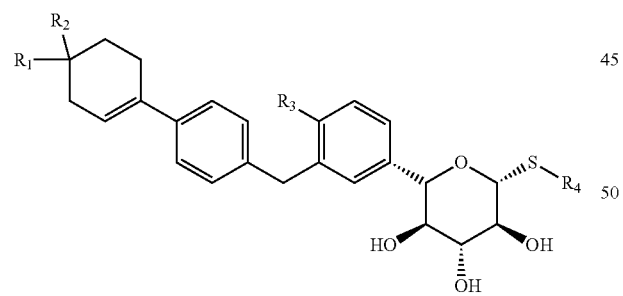

(I-2)

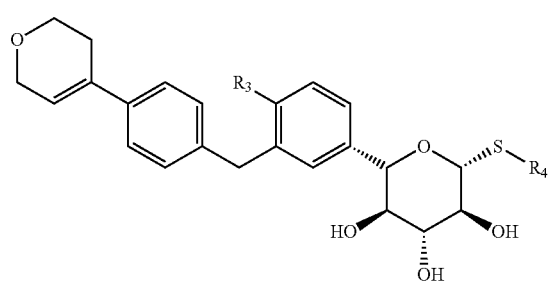

-continued (I-3)

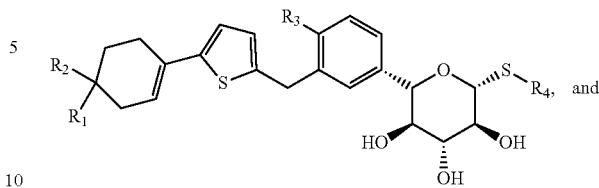
and (I-4)

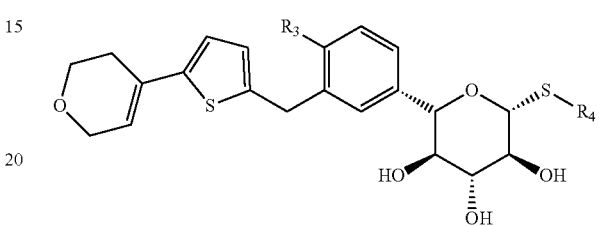

wherein, $R_1$ and $R_2$ are as defined in claim 1;

$R_3$ is as defined in claim 1;

$R_4$ is as defined in claim 1.

10. The compound of the following formula, an isomer thereof, or a pharmaceutically acceptable salt thereof according to claim 1, selected from

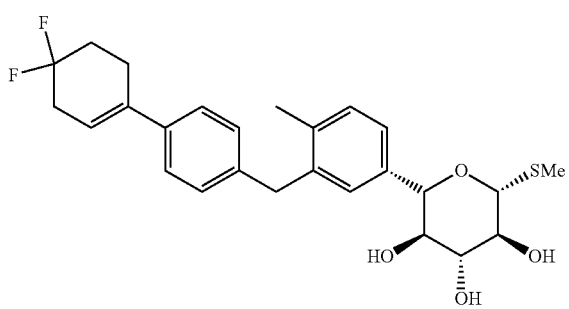

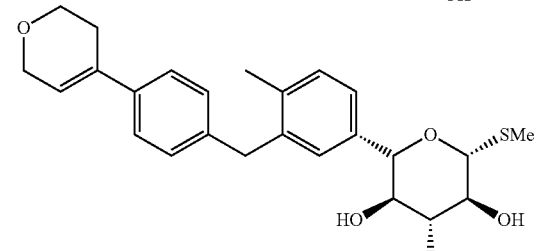

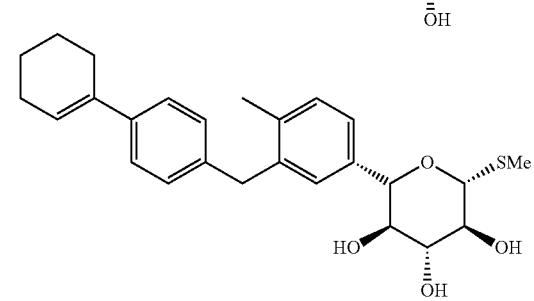

-continued

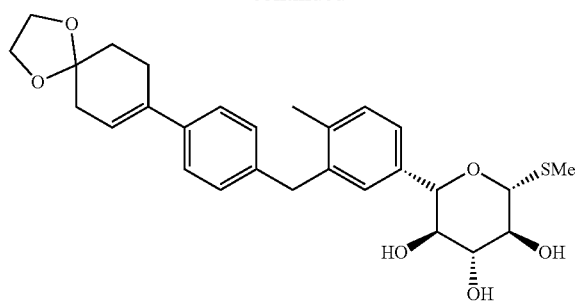
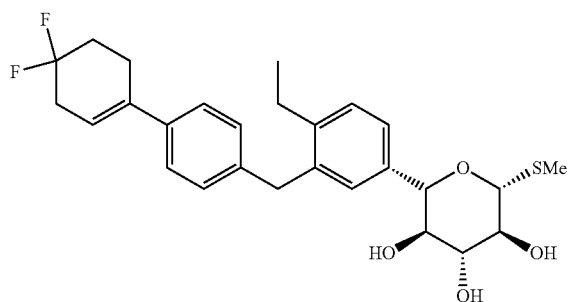
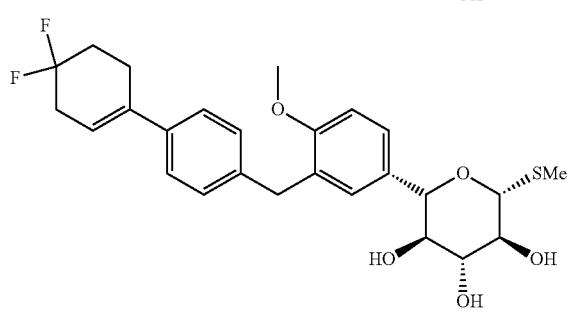
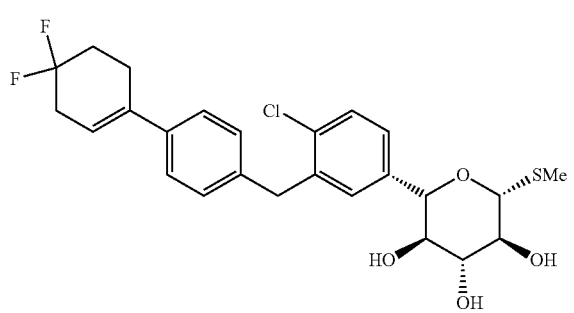

-continued

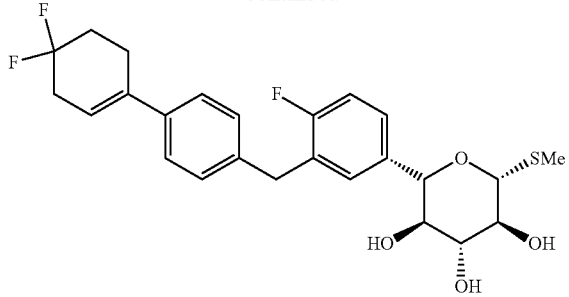
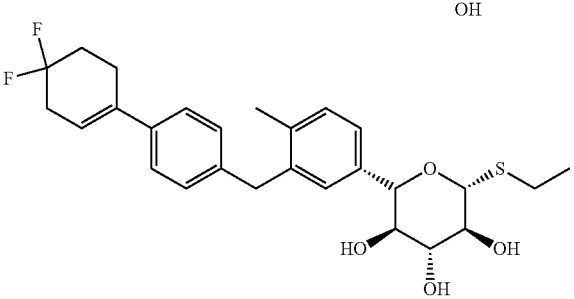
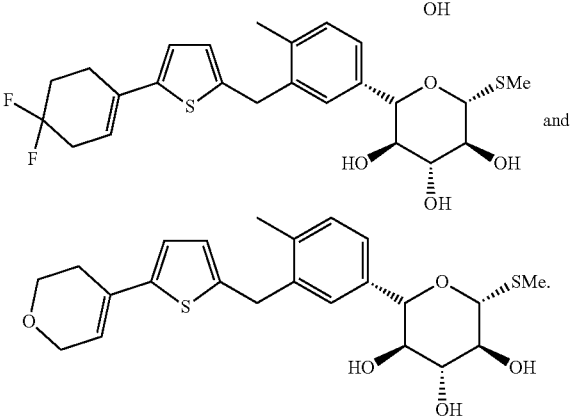

and

11. A pharmaceutical composition, comprising a therapeutically effective amount of a compound, an isomer thereof or a pharmaceutically acceptable salt thereof according to claim 1 as an active ingredient, and a pharmaceutically acceptable carrier.

12. A method for treating SGLT1/SGLT2 related diseases, comprising a step of administering the compound or a pharmaceutically acceptable salt thereof according to claim 1 to a subject in need.

13. The method according to claim 12, wherein the disease is diabetes.

* * * * *